US010582889B2

(12) United States Patent
Pernisa et al.

(10) Patent No.: US 10,582,889 B2
(45) Date of Patent: Mar. 10, 2020

(54) ULTRASOUND APPARATUS FOR ASSESSING THE QUALITY OF A PATIENT'S BONE TISSUE

(71) Applicant: ECHOLIGHT S.R.L., Lecce (IT)

(72) Inventors: Matteo Pernisa, Lecce (IT); Sergio Casciaro, Lecce (IT); Francesco Conversano, Monopoli (IT); Ernesto Casciaro, Lecce (IT)

(73) Assignee: ECHOLIGHT S.p.A., Lecce (IT)

( * ) Notice: Subject to any disclaimer, the term of this patent is extended or adjusted under 35 U.S.C. 154(b) by 118 days.

(21) Appl. No.: 14/081,826

(22) Filed: Nov. 15, 2013

(65) Prior Publication Data

US 2014/0155748 A1 Jun. 5, 2014

Related U.S. Application Data

(63) Continuation of application No. PCT/IB2012/052482, filed on May 16, 2012.

(30) Foreign Application Priority Data

May 16, 2011 (IT) ................ PI2011A0054

(51) Int. Cl.
*A61B 5/00* (2006.01)
*A61B 8/08* (2006.01)
(Continued)

(52) U.S. Cl.
CPC .......... *A61B 5/4509* (2013.01); *A61B 8/0875* (2013.01); *A61B 8/14* (2013.01);
(Continued)

(58) Field of Classification Search
CPC ....... A61B 8/00; A61B 8/5207; A61B 8/5215; A61B 8/5223; A61B 8/0875; A61B 5/4504; A61B 5/4509; G06T 7/0012
(Continued)

(56) References Cited

U.S. PATENT DOCUMENTS 3,521,064 A * 7/1970 Moran ................ G01V 5/101
250/261
4,926,870 A 5/1990 Brandenburger
(Continued)

FOREIGN PATENT DOCUMENTS

| CN | 1040739 A | 3/1990 |
| CN | 201248722 Y | 6/2009 |
| WO | 03/032840 A2 | 4/2003 |

OTHER PUBLICATIONS

Griffiths, Peter R., and Limin Shao. "Self-weighted correlation coefficients and their application to measure spectral similarity." Applied spectroscopy 63.8 (2009): 916-919.*

(Continued)

*Primary Examiner* — Carolyn A Pehlke
(74) *Attorney, Agent, or Firm* — R. Ruschena Patent Agent, LLC

(57) ABSTRACT

An apparatus (100) for assessing the condition of the bone tissue in a patient's bone region (21). The apparatus includes an ultrasound device (11) that transmits/receives ultrasounds along a plurality of ultrasound propagation lines (15$_i$) for the bone region (21), and for receiving in response from the bone region (21) a plurality of raw reflected ultrasound signals (36,38); a device for generating an ultrasound signal, a sonographic image formation device for forming a sonographic image (29) of the bone region (21), starting from the raw reflected ultrasound signals (36,38); a device for extracting at least one frequency spectrum (43.sub.i,44.sub.i,47,48) starting from at least one part of said plurality of raw reflected ultrasound signals (36,38) coming from corresponding points (34) of the bone region (21), each having a plurality of harmonic components.

10 Claims, 10 Drawing Sheets

(51) Int. Cl.
*G06T 7/00* (2017.01)
*A61B 8/14* (2006.01)
(52) U.S. Cl.
CPC .......... *A61B 8/5223* (2013.01); *G06T 7/0012* (2013.01); *A61B 8/485* (2013.01)
(58) Field of Classification Search
USPC ............. 367/21; 382/128–132; 600/437, 443
See application file for complete search history.

(56) References Cited

U.S. PATENT DOCUMENTS

| | | | | |
|---|---|---|---|---|
| 5,902,240 A * | 5/1999 | Ishii | ................... | A61B 8/0875 600/438 |
| 6,328,695 B1 | 12/2001 | Vammen | | |
| 6,468,215 B1 | 10/2002 | Sarvazyan | | |
| 6,776,760 B2 * | 8/2004 | Marmarelis | .......... | A61B 8/0858 600/448 |
| 7,175,597 B2 * | 2/2007 | Vince | ................. | A61B 5/02007 600/443 |
| 2008/0097211 A1 * | 4/2008 | Sarvazyan | ........... | A61B 8/0875 600/449 |
| 2009/0143681 A1 * | 6/2009 | Jurvelin | ............... | A61B 8/0858 600/449 |
| 2012/0232375 A1 * | 9/2012 | Zebaze | ................. | G06T 7/0012 600/407 |

OTHER PUBLICATIONS

Rumsey, Deborah J. Statistics for dummies. John Wiley & Sons, 2011 (content from http://www.dummies.com/how-to/content/how-to-interpret-a-correlation-coefficient-r.html).*
Barkmann, R., et al. "A method for the estimation of femoral bone mineral density from variables of ultrasound transmission through the human femur." Bone 40.1 (2007): 37-44.*
International Search Report in Prior Application PCT/IB2012/052482, dated October 11, 2012.
Writen Opinion of the International Search Authority in Prior Application PCT/IB2012/052482, dated October 11, 2012.
English Abstract from WO90/01903A1 (equivalent to CN1040739A).
Office Action from Chinese Patent Office dated Dec. 3, 2014.
Office Action from Chinese Patent Office dated Jul. 13, 2015.
Translation of third Office Action from Chinese Patent Office issued in response to Amendment filed Sep. 28, 2015.
English Abstract of CN201248722Y dated Jun. 3, 2009.

* cited by examiner

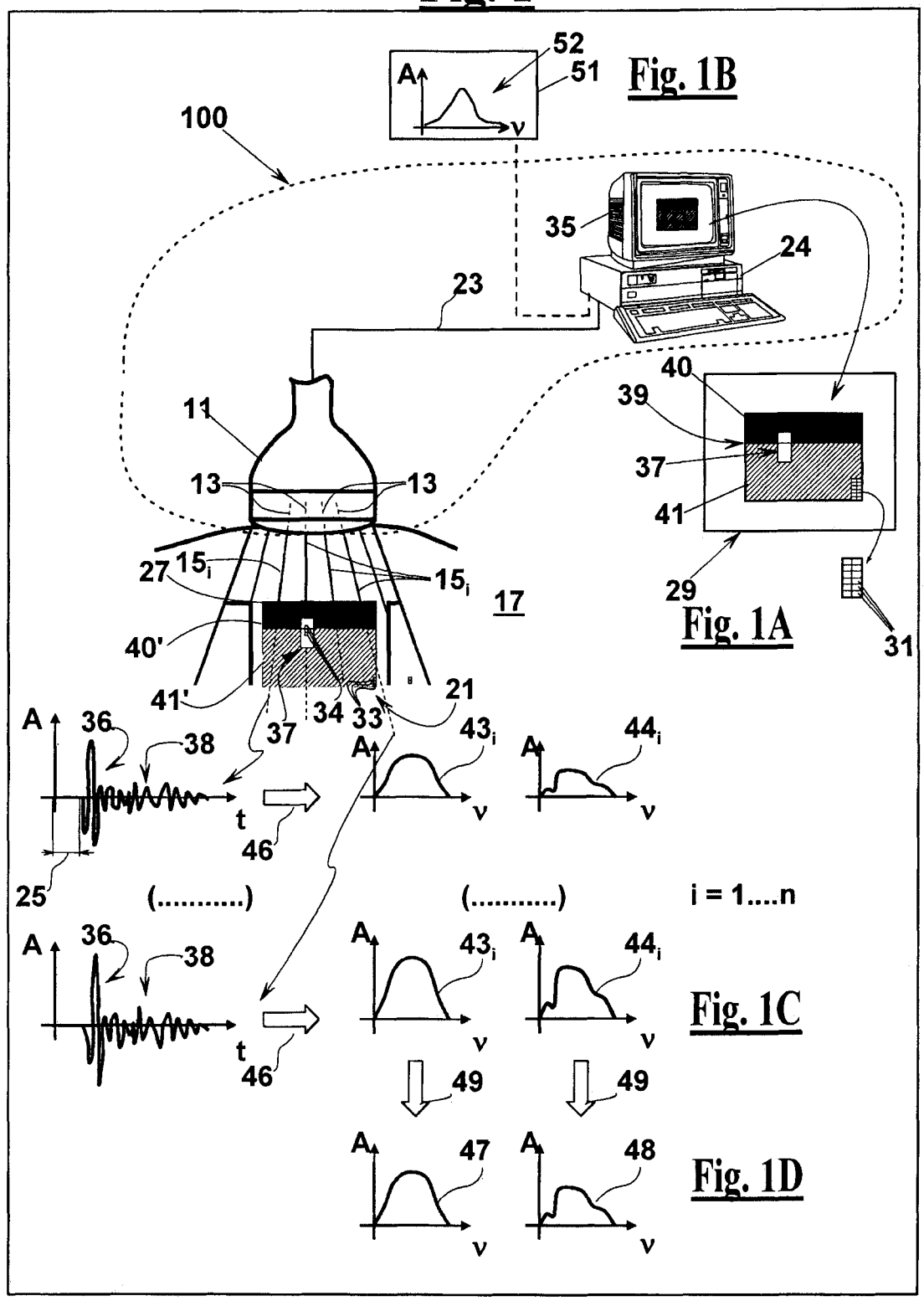

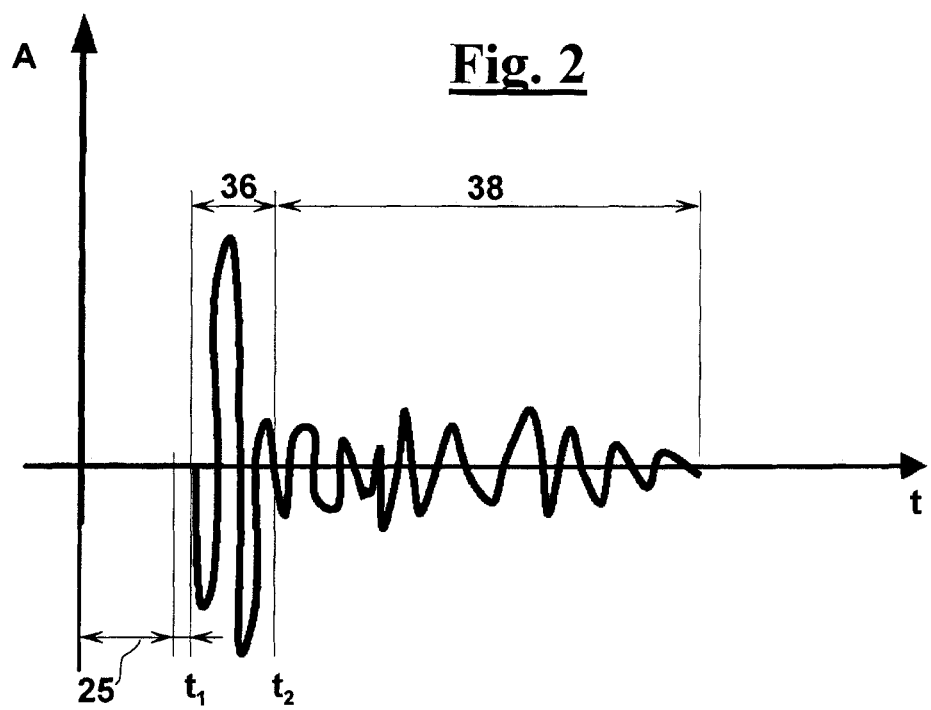
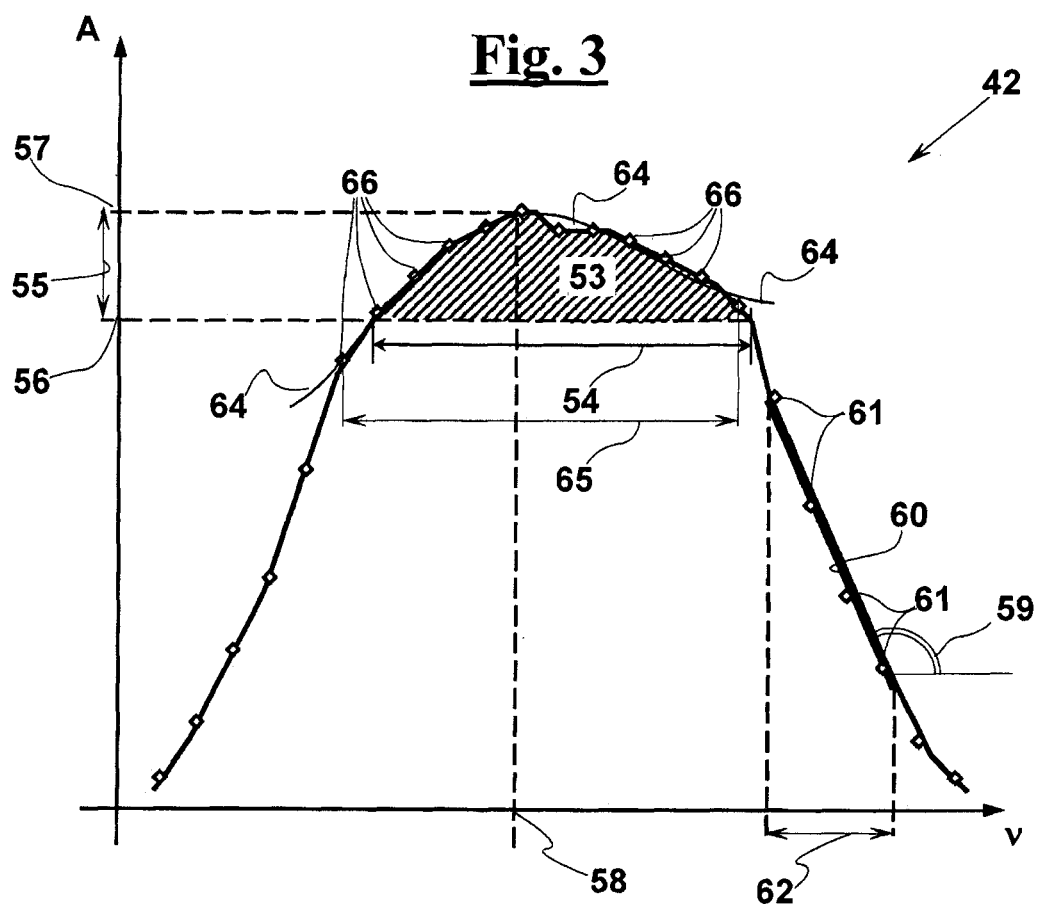

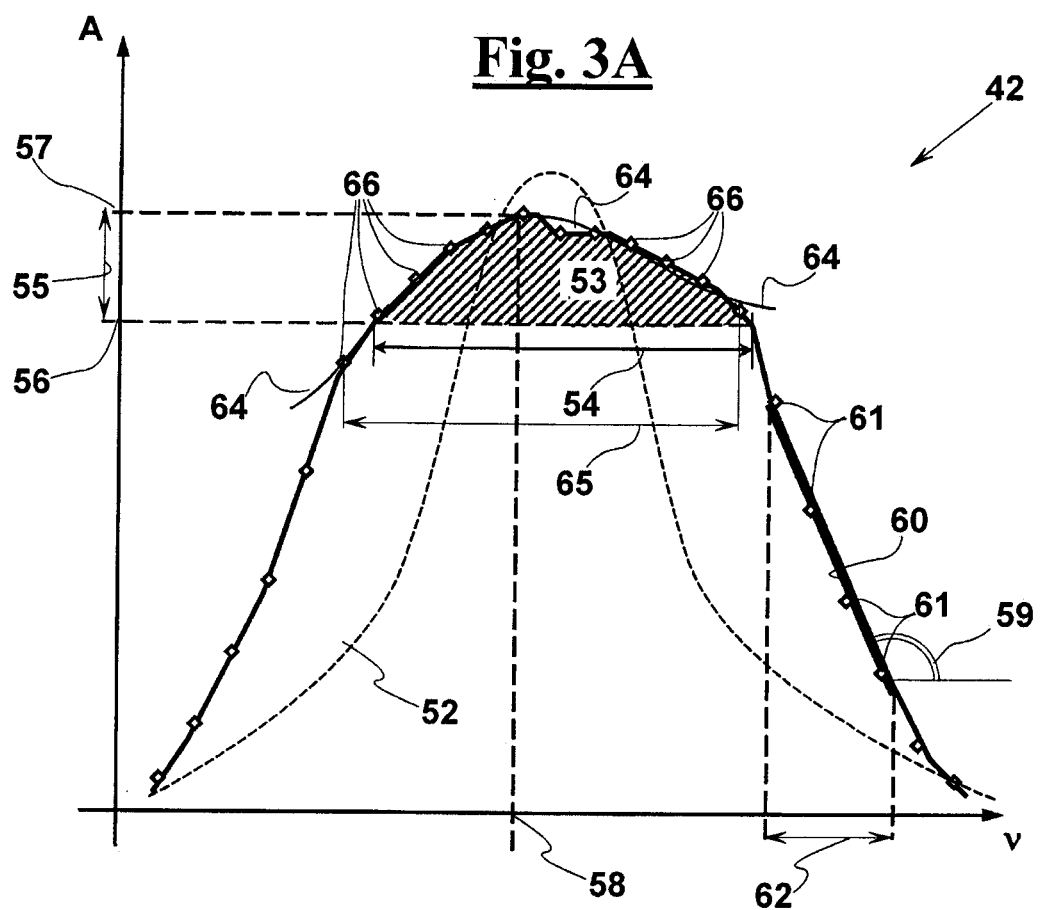

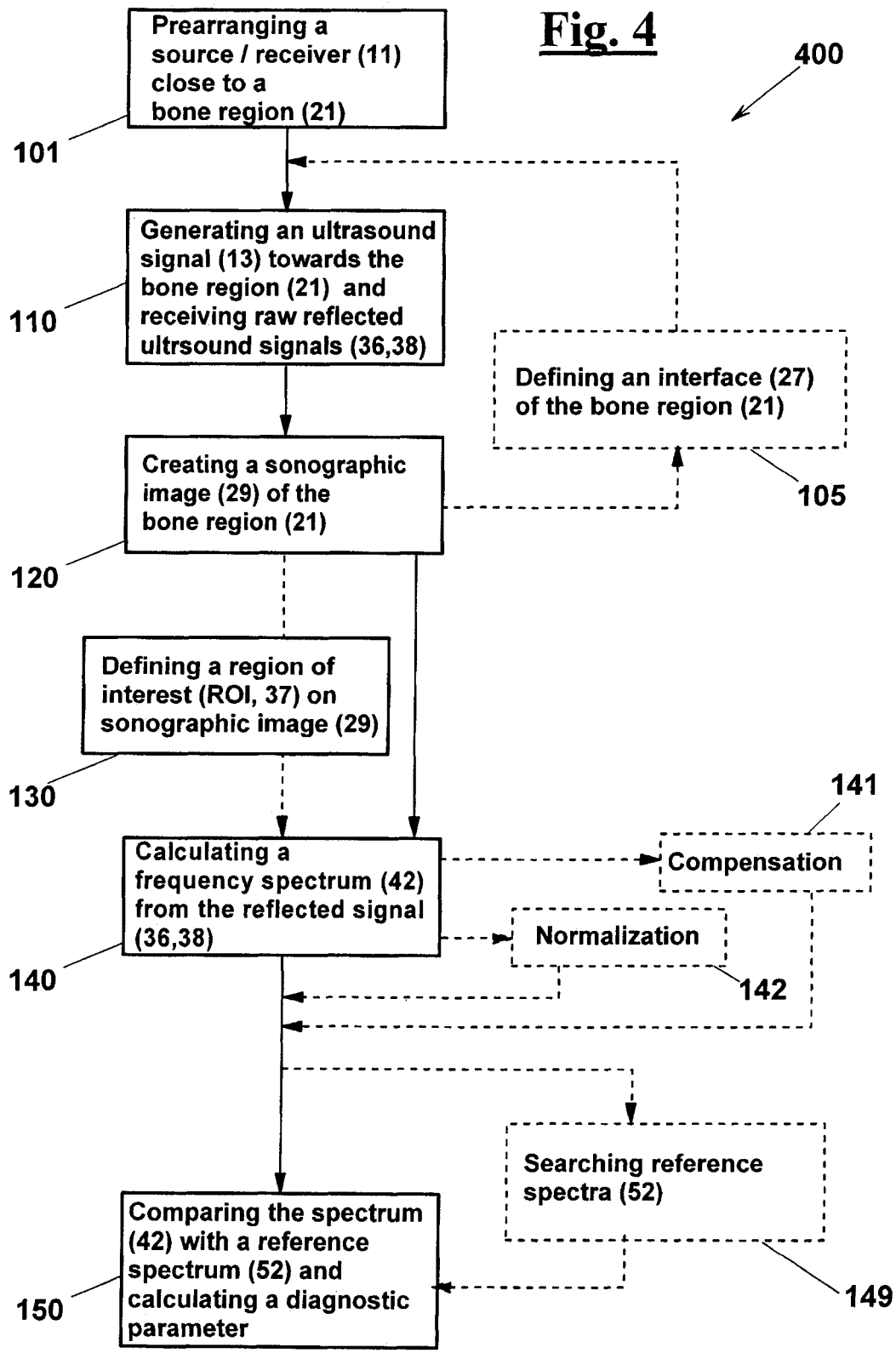

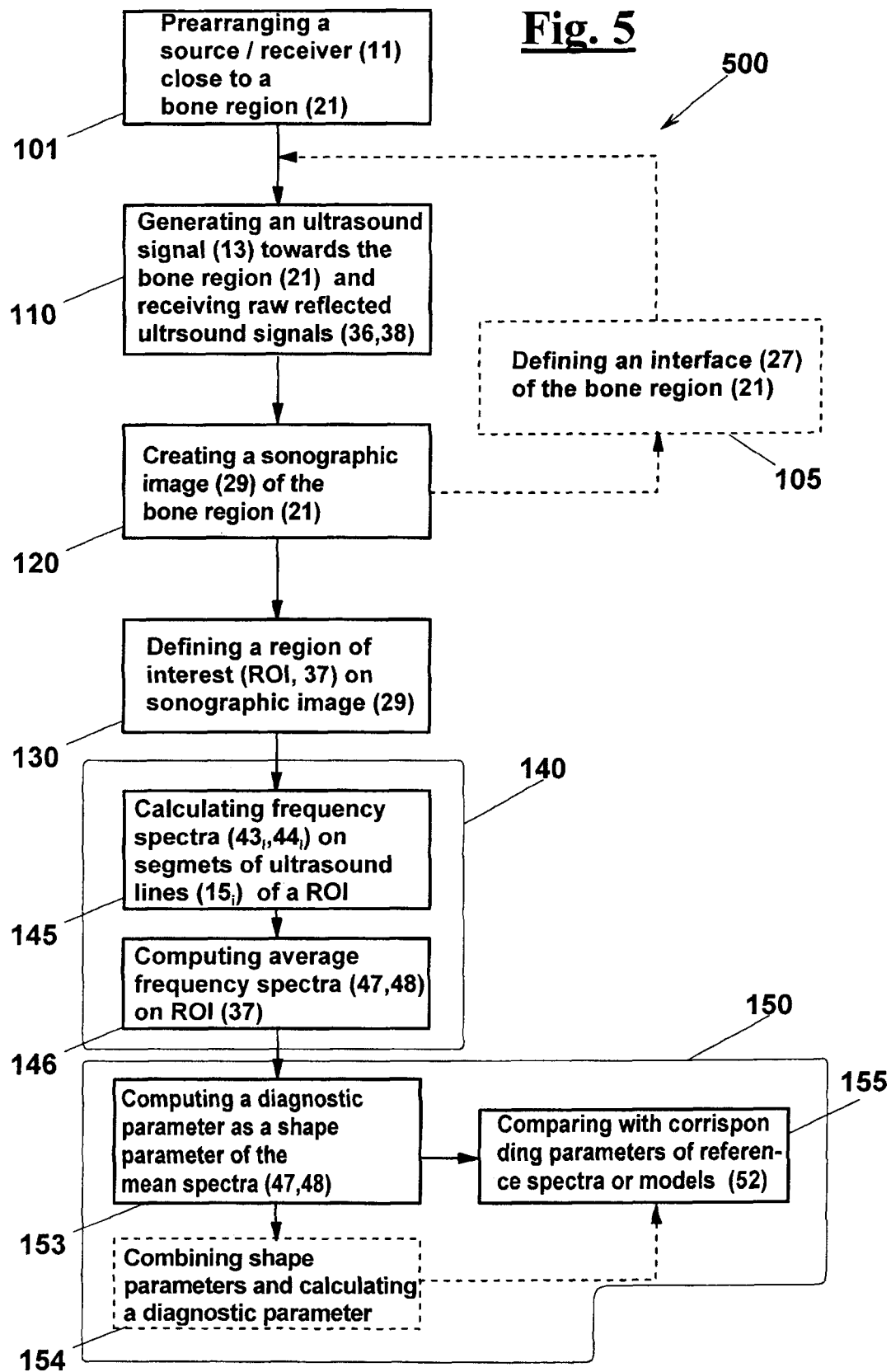

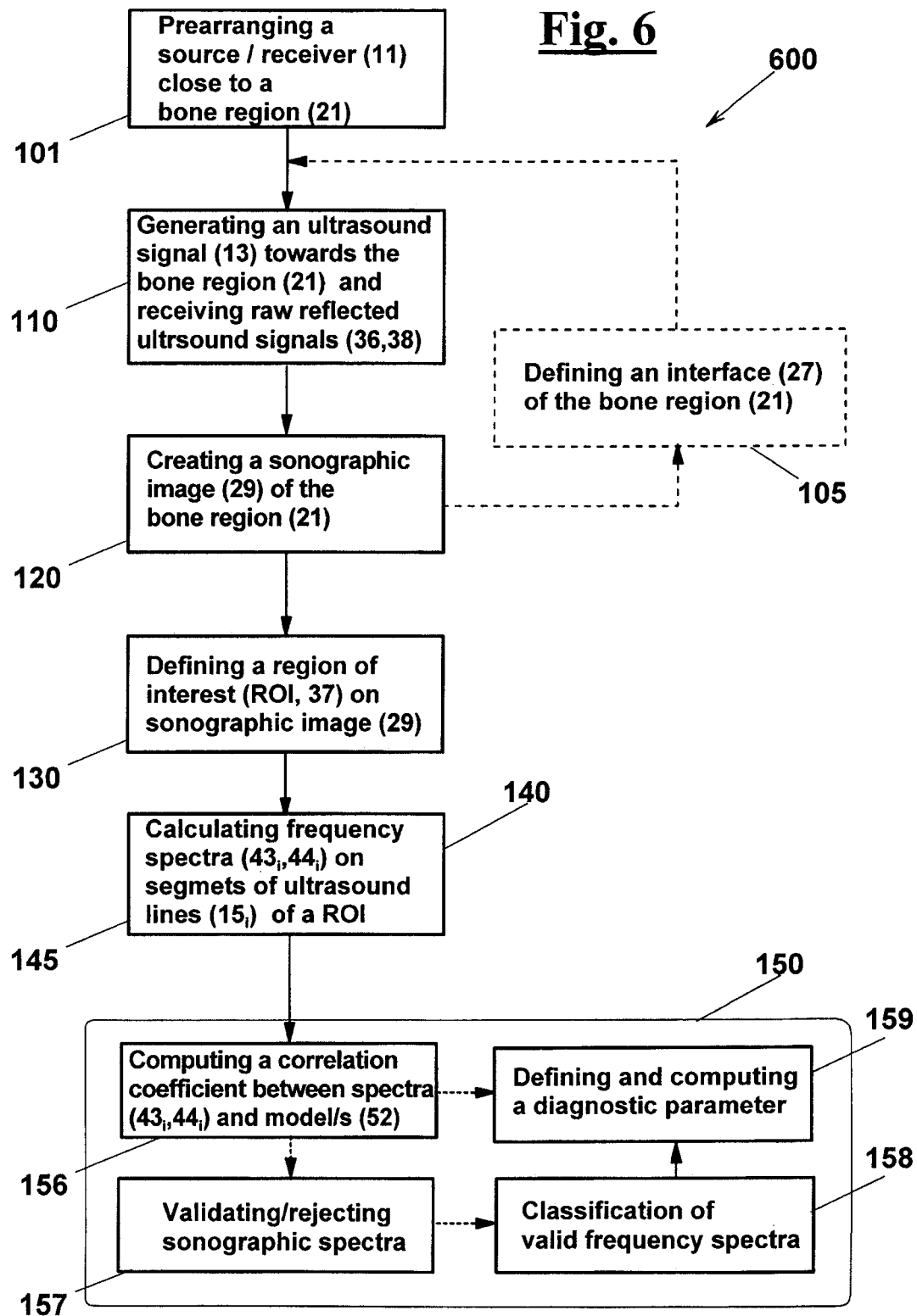

ULTRASOUND APPARATUS FOR ASSESSING THE QUALITY OF A PATIENT'S BONE TISSUE

BACKGROUND OF THE INVENTION

1. Field of the Invention

The present invention relates to an ultrasound apparatus for assessing the condition of the bone structure of a patient. In particular, the apparatus is adapted to carry out bone densitometry tests, i.e. to measure the bone mineral density of a patient's bone region.

2. Brief Description of the Prior Art

The assessment of the condition of the bones of a patient is commonly carried out by measuring the bone mineral density. This assessment, in particular, is used for deciding whether the patient is affected by osteoporosis, and for evaluating the effectiveness of new therapies. The bone mineral density is a parameter that reveals the bone mineral amount. It is particularly important to evaluate the amount of mineral that is present in specific bone regions, such as certain vertebrae and the femur neck.

X-ray techniques are known for evaluating the bone mineral density of a patient. For instance, the DEXA technique (Dual Energy X-ray Absorption) provides causing an X-ray beam to pass through a bone region, and measuring the attenuation of the X-ray beam. This attenuation provides an index of the bone mineral density of the region. An advantage of this technique is that it allows a direct evaluation of the density in any bone region, in particular in the bones that are most likely to fracture from osteoporosis, such as the femur neck and the majority of the vertebrae.

However, the X-ray analysis can provide only a quantitative information about the presence of mineral in the bone network. This depends on how the X-rays interact with the material they pass through. In other words, the X-rays don't allow any structural evaluation of the condition of the bone network. Therefore, the X-rays don't provide any information about the bone structure quality. In particular, the X-ray techniques can't distinguish whether the mineral that is released by drug therapies becomes a part of the bone network and improves the mechanical properties of the latter, or whether this mineral simply fills the gaps present in the network, which grow due to a calcium level decrease, and causes only a slight improvement of bone structural performances. In summary, it is not possible to assess the effectiveness of such therapies by X-ray techniques.

Furthermore, the X-ray techniques involve a relatively long and frequent exposure of the subject to ionizing radiations. For this reason, the diagnostic use of the X-ray techniques is limited by the health regulations. Furthermore, in elderly patients and/or in patients who suffer from various pathologies, the exposure to the X-rays is added to other health risk factors such as further X-ray treatments and exams, drug therapies and the like.

For this and other reasons, ultrasound bone densitometry techniques have been developed, which are known under QUS (Quantitative Ultrasound). These techniques are based on an X-ray transmission through a bone. In other words, an ultrasound signal emitted by an emitter probe passes through a bone region and is collected by a receiver probe located opposite to the emitter probe at the other side of the bone region. The transmitted signal, as received by the receiver, is correlated to the state of the bone tissue on the basis of some quality parameters and of other reference means. Examples of these techniques are described in U.S. Pat. Nos. 5,730,835, 5,218,963, 5,564,423, 6,221,019.

However, since the known ultrasound bone densitometry techniques are based on ultrasound signals used in a transmission mode, they can provide only an indirect and approximate estimate of the mineral content of most parts of the skeleton of a patient. In fact, these techniques are based on measures carried out on peripheral bone regions such as the heel, the phalanx, the radius, the metatarsus, the patella. These bone regions have a small bone thickness, therefore they can be passed through by the ultrasound pulses from one side to the other side, which allows an evaluation by ultrasound pulses in a transmission mode. Furthermore, some bone regions have a conformation which makes it difficult to position the probes for emitting and receiving the ultrasound pulses.

Therefore, the presently known ultrasound techniques don't allow a direct evaluation of the bone mineral density in those bone regions where the osteoporotic disease is particularly critical, such as the majority of the vertebrae and the femur neck, especially in the trabecular part of the bone tissue. These are the regions where the osteoporotic fracture are most likely to occur and/or the most serious. On the other hand, the indirect densitometric evaluation of peripheral sites cannot reliably represent the general condition of a patient, in particular the condition of such most critical regions, since some patients may have locally a mineral level higher than the rest of the skeleton. This is the case, for instance, of people who normally apply much stress on the fingers or on the heels, for sports, professional or other reasons.

Another drawback of the presently known ultrasonic bone densitometry techniques is the interference of the soft tissues that may be present between the probe and some bone regions. For instance, the thickness and the temperature of the skin and of the subcutaneous tissue may be different from a measurement to another and from a patient to another. This sensibly affects the measurement of the ultrasound transmission parameters. For example, the SOS (Speed Of Sound), which is the propagation speed of a transverse ultrasound wave through the trabecular part of the bone (trabecular transverse transmission), does not substantially differ from the SOS through the soft tissues. Moreover, if the temperature of the skin increases, a remarkable reduction of the SOS is observed, for example about 3.6 (m/s)/° C.

To solve partially this problem, a technique and a device for assessing the quality of a bone tissue is known from document WO03/032840, in which a non-linear analysis is used in combination with, or in alternative to shear waves. This technique comprises measuring the speed (pressure wave velocity, shear wave velocity, surface wave velocity) of an ultrasound signal through a bone, between two points of a bone tissue. A speed, which can be related to a bone disease or condition, can be determined from the known distance between the two points, and from the time the signal takes for covering this distance. Firstly, the use of ultrasounds in transmission mode has the general drawback of requiring a couple of sensors, which is uncomfortable when positioning them with respect to each other and to the patient. Furthermore, in some locations that are important for detecting an osteoporotic disease, such as the vertebrae, in particular the lumbar vertebrae, the measurement is complicated by the presence of lateral, spinous and transverse processes. In these bone processes, the cortical tissue prevails over the trabecular tissue, and provides a not very significant diagnostic information, and also provides a noise for the measurement, in particular when assessing a osteoporotic disease in the vertebral body.

Document WO03/032840 (FIG. 6) also teaches and embodiment with a simple reflection and a subsequent following analysis of the nonlinearities of the reflected signals. However, this solution allows only detecting possible bone micro-fractures, and not an osteoporosis condition, since the pathological trabecular tissue has a spongy but substantially homogeneous structure, therefore would not show important nonlinearities.

SUMMARY OF THE INVENTION

It is therefore a feature of the present invention to provide an ultrasound apparatus for determining a quality index of the bone tissue of a patient, i.e. for assessing the condition of the structure of the bone network.

It is also a feature of the invention to provide an apparatus that allows measuring the bone mineral density directly on the bones that have a higher risk of osteoporotic fracture, such as the femur neck and the lumbar and dorsal vertebrae, without using ionizing radiations.

It is a particular feature of the invention to provide such an apparatus that allows observing bone regions in which bone processes would shield the ultrasound field of vision, as in the case of the lower vertebrae.

It is a particular feature of the invention to provide such an apparatus that is not affected by other tissues that are present close to the observed bone region, in particular by soft tissues.

These and other objects are achieved by an apparatus for assessing the condition of the bone tissue in a patient's bone region, the apparatus comprising:

an ultrasound device provided with an ultrasound transceiving means that is configured to emit ultrasound pulses along a plurality of ultrasound propagation lines that can reach the bone region, and to receive raw ultrasound signals from the bone region, in response to the emitted ultrasound pulses, said ultrasound transceiving means comprising an ultrasound signal generation means, which is arranged in the ultrasound transceiving means and configured to generate an ultrasound signal that has frequencies of a frequency range comprising a nominal frequency, the ultrasound transceiving means configured to emit the generated ultrasound signals during a predetermined emission time, a sonographic image formation means for forming a sonographic image of the bone region, starting from the received raw ultrasound signals, the sonographic image formation means displaying the image to allow an operator to identify a zone of the region to be investigated, and to direct the ultrasound device towards the zone;

wherein the ultrasound transceiving means is arranged to transmit the ultrasound pulses and to receive the raw ultrasound signals from a same side of the bone region, such that the received raw ultrasound signals are return raw ultrasound signals reflected by the bone region, whose main feature is that:

a spectrum extraction means is provided that is configured for extracting at least one frequency spectrum starting from at least one part of the return raw ultrasound signals reflected from corresponding points of the bone region, the at least one frequency spectrum having a plurality of harmonic components in which to each frequency of the frequency range an intensity is associated of a portion of one of the raw reflected ultrasound signals that have this frequency, a memory means is also provided that is configured for memorizing at least one reference spectrum associated with at least one healthy and/or pathological subject, and a frequency spectra comparison and diagnostic parameter calculation means is provided for comparing each frequency spectrum, which is extracted by the extraction means, with the at least one reference spectrum recorded in the memory means, and for calculating a diagnostic parameter according to the comparison.

In particular, the extraction means carries out a frequency domain transformation of the raw reflected ultrasound signals, for instance the Fast Fourier transform (FFT).

More in detail, the emitted ultrasound signal penetrates the bone region through a surface that limits the bone region, and reaches points or sites of the bone region at respective depths from the surface, such that in the bone tissues that are present in these sites, respective raw reflected ultrasound signals are formed in response to the emitted ultrasound signal. The raw reflected ultrasound signals are received by the ultrasound device with respective delay times after the emission time, and the delay times depend on the respective depths.

The ultrasound pulses are able to engage with the bone tissue, according to various modes that depend on the structure of the tissue, and allow therefore obtaining information about the bone structure, along with simple bone densitometry data. This is known, for instance, from Claus-C. Glüer, *A New Quality of Bone Ultrasound Research*, IEEE Transactions on Ultrasonics, Ferroelectrics, and Frequency Control, vol. 55, no. 7, July 2008, pp 1524-1528, and from references cited therein. In other words, it is possible to obtain data more detailed than from a simple bone mineral density. As described, the latter is just an index of the presence of a material, and does not provide any information about the structural consistency of the bone tissue. More in detail, the frequency analysis of the interaction between the ultrasound pulses and the bone network allows establishing a correlation between determined harmonic components of the frequency spectrum and the structural features of the bone tissue.

As well known, the osteoporotic disease can seriously affect the stability and can determine a fracture of the vertebral bodies, with severely disabling consequences for the patients that suffer from it. As described above, the presence of the spinous, lateral and transverse processes remarkably limits the accessibility to the vertebral bodies for the diagnostic exams that are carried out via a dorsal approach.

The invention allows therefore easily leaving the soft tissues around the spine out of consideration. Accordingly, it allows to carry out a diagnostic exam of the vertebral bodies via an abdominal approach, in order not to be affected by the vertebral processes.

More in detail, a physician at first can carry out a conventional sonographic procedure using a conventional probe, in order to establish a region of interest. On the basis of the sonographic data alone, the physician can obtain only basic diagnostic data. Then, the invention allows to process raw reflected ultrasound signals and to obtain spectra that are useful if compared with reference models of healthy subjects and of pathological subjects, and to obtain, through the value of at least one diagnostic parameter, information about the bone tissue that could be only in part obtained by X-ray techniques, however with an exposure of the patient to potentially harmful radiations.

The apparatus allows therefore an approach guided by a sonographic image. This is not the case of the prior art ultrasound bone densitometry devices, which use ultrasound beams and measure their attenuation, and do not make reference to the intimate structure of the bone region.

The sonographic image can be obtained conventionally, by means of a conventional probe, which comprise a plurality of piezoelectric crystals. This kind of probe acquires raw reflected ultrasound signals and can be configured to represent these raw signals in the form of a matrix.

As well known, in a matrix representation the raw sonographic signals are arranged in columns and rows. Each column corresponds to a sonographic line or trace, or propagation line of the emitted/reflected sonographic signal. Each row further corresponds to a certain delay time of the acquisition process and therefore, substantially, it corresponds to a certain depth of the points that have generated the raw reflected signals.

The raw reflected signals can be used for building the sonographic image by means of filtering and averaging operations, which leaves out of consideration the detailed information about the bone network within them. The same raw reflected signals, shown in the form of a matrix, are used with their information content to obtain a matrix of spectra for further processing. In other words, the raw reflected signals are compared, with their information content, with reference spectra or data. The sonographic device has therefore a raw reflected ultrasound signals extraction means, i.e. a means for extracting signals that have not been treated yet by the filtration procedure, by an averaging procedure and by other procedures that provide the sonographic image. This approach allows selecting data that are relevant for the analysis.

Furthermore, the apparatus allows carrying out quantitative evaluations on the basis of sonographic data, by a procedure that comprises automatic steps. The prior art devices for performing sonographic investigations of a soft tissue, for instance a cardiac echo-Doppler device, provides sonographic images to be optically analyzed by an operator, who recognizes and defines manually regions of an organ and causes a computer to calculate a geometric parameter of the organ. On the contrary, these devices cannot use these images to provide structural features of the organ. In the case of the bone tissue, where the geometry of the organ is well established, the sonographic apparatus according to the invention allows obtaining structural bone data.

As well known, a bone normally comprises a more compact, cortical surface part, and a trabecular inner part in which cavities are present containing the bone marrow. The ratio between the thickness of the cortical portion and the thickness of the trabecular portion depends on the bone that is considered. For example, long bones, which have a substantially circular cross section, are mainly formed by cortical bone, while the vertebrae mainly consist of trabecular bone. If osteoporosis is present, a reduction of the thickness of the trabeculae (density decrease) and/or a reduction of the cortical part thickness can be detected. An ultrasound signal, while travelling along the bone, progressively changes its own shape, frequency, intensity and propagation speed, according to specific physical features, normally, both of the cortical part and of the trabecular part.

Therefore, the apparatus advantageously comprises an adjustment means for setting a receiving or listening time of the reflected signals, such that reflected signals are received that come from cortical bone regions and/or from trabecular bone regions. In this case, the frequency spectrum extraction means is adapted to extract at least one frequency spectrum selected between a frequency spectrum of a signal reflected by a portion of the cortical part and a frequency spectrum of a signal reflected by a portion of the trabecular part of the bone region.

The ultrasound device may comprise a positioning and/or fixation means for arranging the ultrasound device and the bone region of the patient in a mutual proximity, so that the ultrasound device can emit ultrasound pulses and reach the bone region, and can receive a plurality of raw reflected ultrasound signals from the bone region, in response to the emitted ultrasound pulses.

In an exemplary embodiment of the invention, the apparatus comprises a space selection means that is configured to define a region of interest, or ROI, of the bone region on the sonographic image.

In an exemplary embodiment, the ultrasound device of the apparatus comprises a ultrasound probe that is equipped with a plurality of sonographic crystals arranged to transceive respective ultrasound signals that travel along respective ultrasound propagation lines of a same sonographic plane, and the sonographic image is an image of a plane cross section of the bone region taken along the sonographic plane, such that the image comprises pixels corresponding to points of the bone region that form a network comprising columns of points aligned along respective ultrasound propagation lines, and comprising rows of points at respective depths of the bone region, and the reflected ultrasound signals that come from the points of the rows are received by the probe with respective delay times after the emission time. The ultrasound probe can be a conventional probe, i.e. a probe of the type commonly used for sonographic investigations of soft tissues, as described hereinafter.

In this case, the space selection means for defining a region of interest, also called "ROI", is preferably configured to define such a region of interest that comprises a plurality of points preferably adjacent to a plurality of ultrasound propagation lines, most preferably adjacent to a plurality of ultrasound contiguous propagation lines, in particular the region of interest has a substantially rectangular shape.

Preferably, the means for defining the region of interest is configured to define a region of interest in a cortical region and/or to define a region of interest in a trabecular region.

The ultrasound probe may also be configured to transceive an emitted/reflected ultrasound signal at the same time in a plurality of sonographic planes that form a sonographic space, according to a three-dimensional acquisition process, instead of transceiving in a single sonographic plane.

In an exemplary embodiment, the frequency spectrum extraction means is configured to perform the transformation on raw reflected ultrasound signals that come from points of a segment of an ultrasound propagation line included in the region of interest, such that a frequency spectrum is obtained that is associated with the ultrasound propagation line, more in particular, that is associated with such segment of an ultrasound propagation line.

In particular the frequency spectrum extraction means is configured to extract a spectrum of at least one segment of an ultrasound propagation line selected between a segment of an ultrasound propagation line included in a region of interest defined in the cortical part of the bone region and a segment of an ultrasound propagation line included in a region of interest defined in the trabecular part of the bone region.

In an exemplary embodiment, the frequency spectrum extraction means is configured to extract a frequency spectrum associated with a region of interest, starting from a plurality of spectra associated with segments of the ultrasound propagation lines included in the region of interest. For example, the frequency spectrum pertaining to a region of interest is computed by calculating, for each frequency, a mean value, for example an arithmetic mean value, of intensity values of the spectra associated with segments of ultrasound propagation lines included in said region of interest.

Preferably, the frequency spectrum extraction means is configured to perform a step of compensating the frequency spectrum pertaining to the segment of the ultrasound propagation line or a step of compensating a spectrum averaged on a ROI. Preferably, the compensation step is carried out by multiplying the reflected signal intensity of each of the harmonics, which correspond to respective frequencies, by respective compensation coefficients. In particular, the compensation coefficients increase with the frequency, from a value close to one, which corresponds to the nominal frequency, to a maximum value, which corresponds to a frequency different from the nominal frequency, and they can be obtained by the transfer function of the ultrasound probe in use, which is a sensitivity feature of the probe. This way, it is possible to take into account the features of the specific receiving range of the transducer used by the receiving means, in particular of the ultrasound probe.

The frequency spectrum extraction means may also be configured to calculate the frequency spectrum pertaining to a volume of the bone region starting from the spectra of regions of interest that belong to a plurality of sonographic planes, in particular, by calculating an average spectrum of spectra of plane regions of interest.

Said frequency spectrum extraction means may also be configured to perform a step of a normalizing the frequency spectrum pertaining to the segment of an ultrasound propagation line, or to perform a step of normalizing a frequency spectrum on a ROI by shifting the mean frequency spectrum in such a way that the maximum value of the intensity of the spectrum is 0, and that the intensity values lower than the maximum value are negative, wherein, for instance, the intensity values are expressed in dB.

In particular, the diagnostic parameter can be correlated to the bone mineral density, on the basis of reference tests carried out by means of devices that are considered the "gold standard", for example X-ray devices.

The apparatus according to the invention allows therefore carrying out a comparative evaluation of the bone mineral density, without using ionizing radiations, which are potentially harmful for the patient. This evaluation can be carried out on substantially any bone region, in particular on bone regions that are particularly critical, since they are likely to experience an osteoporosis risk, such as the majority of the vertebrae and the femur neck. In other words, the apparatus according to the invention does not have the drawbacks of the prior art methods, which are based on ultrasound pulses in transmission mode and allow a comparable evaluation only on low-thickness bone regions in which the use of ultrasound pulses in transmission mode is possible, and which cannot represent the mineral content of the subject's bone tissue.

In a particular exemplary embodiment, the frequency spectra comparison means is configured to calculate this diagnostic parameter as a shape parameter of said at least one frequency spectrum, or as a combination of a plurality of shape parameters.

In particular, the shape parameter or the shape parameters are selected from the group consisting of:

an area defined by the frequency spectrum within a predetermined range of frequencies or of amplitudes;

a width of the frequency spectrum at a predetermined amplitude level, in particular at a level defined by an amplitude value that is lower by 3 dB, or by 1 dB, than a maximum value of the frequency spectrum;

a frequency corresponding to a maximum value of the frequency spectrum;

a slope of a line that interpolates points of the frequency spectrum within a predetermined range of frequencies;

the coefficient of a polynomial that interpolates points of the frequency spectrum within frequencies that contain a frequency corresponding to a maximum value of the frequency spectrum;

a ratio of physical quantities that can be deducted from the frequency spectrum.

The analysis and of calculation means can be configured to calculate any parameter that is adapted to describe the shape of the spectrum or of a mathematic representation of it, for instance a representation obtained by ICA, Wawelet processes, and the like.

In another particular exemplary embodiment, the frequency spectra comparison and diagnostic parameter calculation means is configured to calculate a correlation coefficient between a plurality of frequency spectra and a reference spectrum, or a portion of said reference spectrum that corresponds to the portion of the mean frequency spectrum, of a healthy subject and/or of a pathological subject, and is configured to calculate the diagnostic parameter according to the correlation coefficient. In particular, the correlation coefficient is a Pearson's correlation coefficient.

In an exemplary embodiment, the frequency spectra comparison means is configured to:

calculate respective correlation coefficients with the at least one reference spectrum of a plurality of frequency spectra that are associated with respective segments of ultrasound propagation lines (i) included in the region of interest, and to select a set of valid frequency spectra, wherein at least one of the correlation coefficients exceed a predetermined threshold value;

calculate a percentage of healthy valid spectra or of pathological valid spectra or of intermediate valid spectra, wherein one of the valid spectra is a healthy spectrum or a pathological spectrum or an intermediate spectrum according to whether the correlation coefficient with the healthy or with the pathological or with the intermediate model, respectively, is substantially higher than the correlation coefficient with the other pathological models;

define a diagnostic parameter.

For example, the diagnostic parameter may be the percentage of healthy, or pathological, or intermediate valid spectra, respectively. In alternative, the diagnostic parameter may be more specific, in other words it may take into account the values that have valid correlation coefficients: for instance, this parameter may depend on the mean value of the correlation coefficients of the valid spectra, in particular it may be the complement to 1 of the mean value of the correlation coefficient of the valid spectra. In alternative, the correlation coefficient me be, or may depend upon, a statistic parameter or a combination of statistic parameters that describe/s the distribution of the valid spectra correlation coefficients.

Preferably, the apparatus has an access to a reference spectra database and/or to a database of reference diagnostic parameters database values, said reference spectra/diagnostic parameters values known as disease indexes i.e. as indexes of disease seriousness, of healthy and/or pathological subjects.

The frequency spectra comparison and diagnostic parameter calculation means may be configured to define as the diagnostic parameter a diagnostic parameter of a reference spectrum selected among a plurality of reference spectra that represent specific pathology seriousness levels.

Advantageously, the apparatus has a database selection means, associated to the access to the database, for selecting a portion of the database that comprises spectra and/or reference values of subjects for whom at least one of the following parameters:
- age range;
- sex;
- ethnic origin;
- a pathological condition.

is the same as in the patient.

In particular, the correlation coefficient is a Pearson's correlation coefficient, and said threshold value is selected between 0.7 and 0.8, more in particular, said threshold value is about 0.75.

In particular, the frequency spectra comparison means is configured to calculate the diagnostic parameter between T-score and Z-score, wherein:
- T-score is calculated by computing the difference between the value of the diagnostic parameter (BMD, bone mineral density) and the average value (BMD)' of the same parameter as evaluated for subjects of the same sex but of an age at which the peak bone mass value occurs (typically, 30 years), and dividing the result of this difference by the standard deviation a' of the values of the parameter measured for the subjects at the peak bone mass value, i.e. T-score is calculated by the formula:

$$T\text{-score}=[(BMD)-(BMD)']/\sigma'$$

- Z-score is calculated by computing the difference between the value of the diagnostic parameter (BMD) and the average value (BMD)" of the same parameter measured for subjects of the same sex and of the same age of the patient, and dividing the result of this difference by the standard deviation $\sigma''$ of the values of the parameter measured for subjects of the same age as considered, i.e. Z-score is calculated by the formula:

$$Z\text{-score}=[(BMD)-(BMD)'']/\sigma''$$

Such disease condition may be classified according to the definition of the World Health Organization (WHO), based on the T-score value:
- T-score>−1: normal bone mineral density, i.e. absence of signs of disease;
- −2.5<T-score<−1: osteopenia, i.e. the skeleton has a reduced mineral bone density with respect to the peak bone mass value, but an overt osteoporosis is not yet present;
- T-score<−2.5: osteoporosis.

The emitted sonographic signals can have frequencies set preferably between 0.2 MHz and 30 MHz.

As described above, the source of ultrasound signals, or the probe, is configured to emit ultrasound signals of frequencies set in a frequency range that has a predetermined amplitude, the frequency range comprising a nominal frequency, for example a nominal mean frequency. Preferably, the nominal frequency of the emitted ultrasound pulses is set between 2 and 9 MHz, in particular it is selected among 3.5, 5 and 7.5 MHz.

In a particular exemplary embodiment, the space selection means of the apparatus comprises a surface recognizing and/or defining means for recognizing and/or defining a limiting surface of the bone region. This way, it is easier to investigate the bones that have a shape complicated by the presence of bone protrusions or processes, which are normally unimportant for the purpose of the investigation. In fact, the surface recognizing and/or defining means for identifying/defining the limiting surface of the bone region makes it possible to exclude from the sonographic acquisition, i.e. from the bone region to investigate, these unimportant bone portions, for example the spinous processes of the vertebrae, typically of the lumbar and of the dorsal vertebrae. Similarly, it is possible to exclude portions of tissue different from bone tissue from the sonographic acquisition. This is particularly advantageous if an abdominal sonographic approach to the spinal column is not useful, due to the presence of thick tissue layers, for example in the case of a fat subject, and a posterior approach is therefore necessary, i.e. an access through the region towards which the spinous processes extend.

Advantageously, the apparatus comprises a nominal frequency adjustment means and/or of a frequency range amplitude adjustment means and/or an acoustic pressure adjustment means. This way, it is possible to obtain a frequency spectrum that can be used to investigate more in detail specific harmonics that can be of particular interest for a given subject. In particular, the adjustment means may be a selection means for selecting the frequency and/or the amplitude and/or of the acoustic pressure among respective predetermined values, to be selected responsive to the features of the subject. This is advantageous since, unlike the case of soft tissues, the response of the bone tissue to the ultrasound pulses depends typically upon such factors as the age, the sex, the ethnic origin, as well as pathological factors, in other words, a bone having a determined disease can be investigated more accurately if different frequencies are used. The possibility to adjust the acoustic pressure makes it possible to take into account that the response of the bone tissue to the ultrasound pulses may depend more or less on such factors as the presence of fat tissue.

Advantageously, the space selection means for defining a region of interest is configured to define and to recognize at least one anatomical reference point of the bone region, and to identify during a measurement session a region of interest that coincides with a previously defined region of interest, said previously defined region of interest defined in a previous sonographic session, on the basis of the at least one anatomical reference point.

This way, the apparatus allows automatically monitoring the evolution of a region of interest. This makes it possible to compare more accurately the conditions of a same bone of a patient at time intervals, for instance at intervals of one year from an evaluation to the next one, and therefore to evaluate the effectiveness in the time of a drug or of another therapy for improving the bone resistance, which is evaluated both as bone network quality, and as an increase of the mineral of the bone network.

In a preferred exemplary embodiment, said memory means configured for memorizing at least one reference spectrum comprises a computation means for computing said reference spectra that is configured to:
- select a sonographic frame containing a bone region to be used as a model;
- obtain an overall trabecular spectrum of said region and of sub-regions of said region, in particular said trabecular spectra are compensated and normalized;
- for each sub-region, identify an interface of the vertebra to be investigated;

generate a bundle of ultrasound propagation lines that meet the interface as defined above;

on each radiofrequency signal that is associated with one ultrasound propagation line of the above bundle, selecting a portion corresponding to the reflection provided by a trabecular region of the bone;

calculate a spectrum, for example by FFT, for each of the above signal portions;

advantageously, compensate each spectrum, in order to take into account the probe receiving range characteristics;

advantageously, normalize each spectrum with respect to its own maximum value, in particular, in such a way that its maximum value becomes 0 dB;

calculate an average spectrum of all the single spectra that have been defined by the above signal portions.

In an exemplary embodiment, for each spectrum defined by a respective signal portion, a correlation coefficient is calculated, for example the Pearson's correlation coefficient, for correlating this spectrum of a respective signal portion, and the mean spectrum;

among all the spectra defined by the portions of said signal, select the spectra for which the correlation coefficient with the average spectrum is higher than a minimum reference value, in particular select the spectra for which the Pearson's correlation coefficient is higher than 0.900;

calculate a further average spectrum of the spectra that have a correlation coefficient exceeding the minimum value;

for each spectrum $S_i$ defined by a respective signal portion, calculate a further correlation coefficient, for example the Pearson's coefficient for correlating the spectrum defined by a respective signal portion and the average spectrum of the spectra the correlation coefficient of which exceeds a minimum value;

among all the spectra defined by respective signal portions, select further spectra that have a correlation coefficient with the average spectrum of the spectra for which the correlation coefficient exceeds the minimum value is, in turn, higher than this minimum value, in particular further spectra that have a Pearson's coefficient r>0.900. The number of such selected spectra can be higher than, lower than or the same as, the number of the previously selected spectra;

calculate a further average spectrum of the selected further average spectra;

repeat the step of computing said new correlation coefficient, selecting said further spectra and computing the further correlation coefficient until a final average spectrum is obtained such that:

each of the remainder spectra $Sn_i$ that is included in the final average spectrum has a correlation coefficient for correlating the final average spectrum higher than the minimum value, in particular it has a Pearson's correlation coefficient r>0.900;

each other spectra $S_i$ that is not included in the final average spectrum has a correlation coefficient for correlating the final average spectrum lower than or the same as the minimum value≤0.900.

In other words, the procedure is discontinued when a further repetition of the procedure would produce a spectrum that coincides with the last calculated one.

In particular, the model bone region may be a vertebra, in particular a lumbar vertebra, and the computation means for computing said reference spectra are configured to:

repeat the previous steps for other three vertebrae, in particular three lumbar vertebrae, finally obtaining four final spectra, one for each of the above vertebrae;

calculate a mean vertebral final spectrum of the four final spectra.

The final vertebral average spectrum represents the contribution of the subject considered to the model, obtained as an average of all the mean vertebral final spectra of a population of subjects who take part to the model, for a corresponding category of subjects.

BRIEF DESCRIPTION OF THE DRAWINGS

The invention will be now shown with the description of an exemplary embodiment thereof, exemplifying but not limitative, with reference to the attached drawings, wherein:

FIGS. 1A-1D diagrammatically show an apparatus, according to the invention, for assessing the condition of the bone tissue in a patient's bone region, and the relative operation, in particular:

FIG. 1A shows a display means associated to the apparatus according to the invention;

FIG. 1B shows a reference spectrum for frequency spectra extracted and used by the apparatus according to the invention;

FIG. 1C shows frequency spectra associated with respective ultrasound propagation lines, said frequency spectra extracted and used by the apparatus according to the invention;

FIG. 1D shows frequency spectra associated with ROIs or ROI portions, said frequency spectra calculated and used by the apparatus according to the invention;

FIG. 2 diagrammatically shows a time plot of sonographic signals received from the bone region that is investigated in response to sonographic signals coming from the ultrasound probe of an apparatus;

FIG. 3 shows an example of frequency spectrum of a sonographic signal that can be obtained by means of the apparatus and of the process diagrammatically shown in FIG. 1, and also shows some shape parameters;

FIG. 3A shows an example of frequency spectrum of a signal and one or more reference or sample or model frequency spectra;

FIG. 4 is a block diagram of a first process for assessing the condition of the bone tissue in a patient's bone region that can be carried out with the apparatus of FIG. 1;

FIGS. 5 and 6 are block diagrams that relate to particular methods for assessing the condition of the bone tissue in a patient's bone region;

FIG. 10 is a diagram that shows the correlation between the BMD estimated by the ultrasound system and the BMD measured by the DXA system, for all the patients of the population which includes the category FIGS. 7-9 relate to;

FIG. 11 is a diagram that shows the correlation between the T-score estimated by the ultrasound system and the T-score calculated by the DXA system, for the patients which FIG. 10 is related to;

FIG. 12 is a diagram that shows the correlation between the Z-score estimated by the ultrasound system and the Z-score calculated by the DXA system, for the patients which FIG. 10 is related to;

DETAILED DESCRIPTION OF THE PREFERRED EMBODIMENTS

Figure 7:
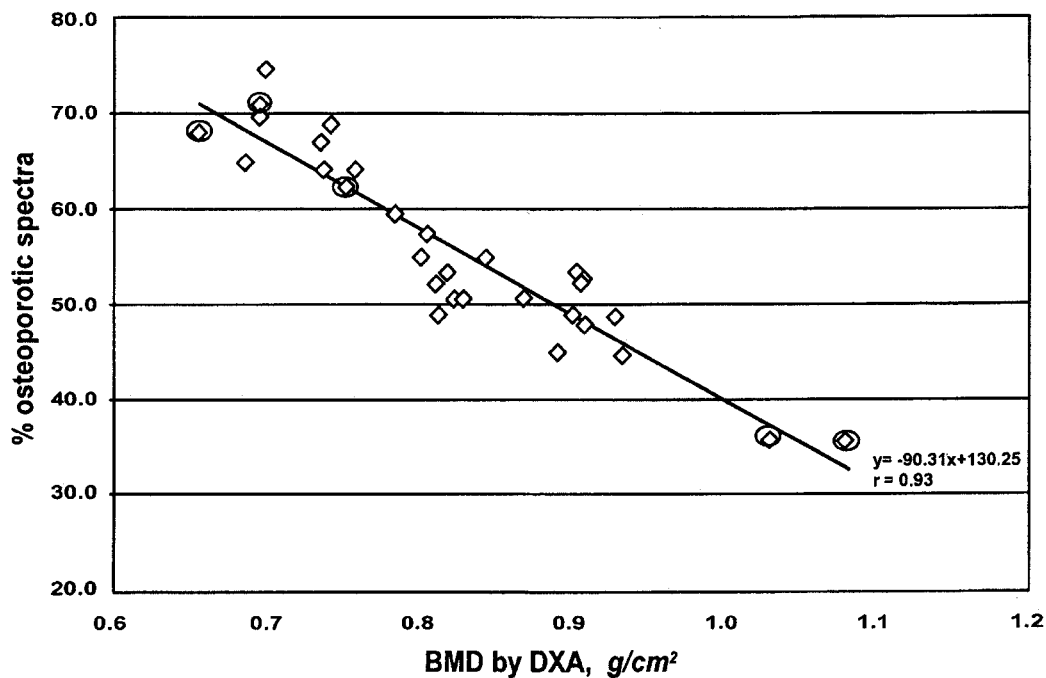
FIG. 7 is a diagram of a diagnostic parameter of a homogeneous category of a population of patients, plotted versus the BMD (bone mineral density) evaluated by the DXA system.

With reference to FIG. 1, an ultrasound apparatus 100 is described according to an exemplary embodiment of the invention, for assessing a patient's bone structure condition. Apparatus 100 comprises an ultrasound device that, in an exemplary embodiment as shown, comprises a ultrasound probe 11, which is equipped with an ultrasound transceiving means suitable for transmitting/receiving ultrasound signals along a plurality of ultrasound propagation lines $15_i$. Ultrasound probe 11 is configured to work as a source and as a receiver of ultrasound signals. Ultrasound probe 11 has an array of n sonographic crystals, in particular of piezoelectric crystals, for emitting and for receiving ultrasound signals 13 in a predetermined frequency band v, about at a nominal frequency v*. Ultrasound probe 11 is configured to emit ultrasound signals 13 according to respective ultrasound propagation lines $15_i$ arranged in a same plane 17 which is, for instance, the plane of the sheet of FIG. 1. Hereinafter, "i" indicates an integer number that may range between 1 and a number of sonographic crystals n. Hereinafter, whenever subscript "i" appears, it is meant that the corresponding value can range between 1 and n, with the above indicated meaning. Ultrasound probe 11 can be a conventional probe. For instance, ultrasound probe 11 can be an abdominal CONVEX probe type, which is easily available on the market.

In a particular exemplary embodiment, probe 11 may comprise a means, not shown, for adjusting and/or for selecting the nominal frequency v*, for instance, between 3.5, 5 and 7.5 MHz, as well as for selecting the amplitude of the frequency band, and/or for selecting the acoustic pressure.

In a particular exemplary embodiment, probe 11 may comprise a means, not shown, for adjusting and/or for selecting the amplitude and/or the acoustic pressure of the emitted signal, within a predetermined set of values.

Apparatus 100 comprises a mutual positioning means of probe 11 and of a bone region 21 of the patient, such that bone region 21 returns a reflected ultrasound signal that can be received by probe 11 when this operates as a receiver, in response to the ultrasound signal emitted by probe 11 when operating as a source. As diagrammatically shown in FIG. 1, the bone region, for example a lumbar vertebra 21 or a portion thereof, comprises an external cortical part 40' and an internal trabecular part 41'. Therefore, the latter is located at a distance from probe 11 higher than cortical part 40'.

Ultrasound probe 11 has an own power supply or a connection to an external power supply, not shown. Moreover, ultrasound probe 11 has a connection 23 for a computer 24, which comprises a program means for driving an acquisition process of reflected signals, and for analyzing the reflected signals. In particular, a program means is provided for defining an operation mode of probe 11 as a source of ultrasound pulses, in which the probe is configured to generate an ultrasound signal during a predetermined emission time 25. A program means is also provided for defining an operation mode of probe 11 as a receiver of ultrasound signals that are reflected by regions located at different depths within the bone tissue of region 21, in response to emitted signal 13. The reflected ultrasound signals, coming from a respective region depth, are received by probe 11 after a delay time that depends on this respective depth, with respect to a border surface 27 of bone region 21.

In an exemplary embodiment of apparatus 100, computer 24 comprises a program means for adjusting the time during which the reflected signals are received or listened, in order to decide whether signals will be detected coming from regions of cortical part 40' of bone region 21 and/or coming from regions of trabecular part 41' of bone region 21.

Computer 24 has a sonographic software that is configured to acquire electric signals from probe 11 which have an intensity A that is proportional to the intensity of the raw reflected signals coming from points 33 of bone region 21 and received by probe 11. The sonographic software is configured to transform these electric signals, by a conventional method, into image parameters, typically into gray levels of a gray scale, in order to generate a sonographic image 29 of bone region 21. Sonographic image 29 comprises a matrix 31 of pixels that are associated with respective points 33 of the observed region. Such image can be seen by an operator by a conventional display means, as a monitor 35, the image of which is shown enlarged in FIG. 1A.

Apparatus 100 may comprise a space selection means for defining a region of interest or ROI 37 according to sonographic image 29, for assessing the patient's bone structure condition. This space selection means may comprise a touch-screen interface portion of monitor 35, or a means for selecting an image portion 37 on sonographic image 29, which corresponds to the region of interest, by introducing coordinate domains or by using a conventional pointing device.

In a particular exemplary embodiment of apparatus 100, computer 24 comprises a program means for autonomously defining or recognizing a ROI 37 in bone region 21, possibly starting from determined anatomical reference points, defined in bone region 21, where the position of ROI 37 is defined with respect to the reference point. In particular, the program means is configured to recognize the anatomical reference points, or directly the ROI 37, as a particular pattern of gray levels about one point, according to a pattern model predefined as a typical pattern of an anatomical reference point either of a ROI, or of a distribution defined as an anatomical reference point, or directly as a ROI in a previous acquisition of the same bone region 21.

Computer 24 may also comprise a means for automatically determining a border line 39 between portion 40 and portion 41 of sonographic image 29, corresponding to cortical part 40' and to trabecular part 41', respectively, of bone 21. As shown more in detail in FIG. 2, cortical part 40' provides reflected signals 36 that are received by probe 11 after a delay time set between a time $t_1$ and a time $t_2$, which have intensities A normally higher than signals 38 coming from the trabecular region, which are received by probe 11 after a delay time longer than $t_2$. The means for determining border line 39 are advantageously configured to recognize time $t_2$, after which reflected signals are received, coming from points of the trabecular region 41', of a lower intensity A with respect to the reflected signals received before time $t_2$, which comes from points of the cortical region 40', and are advantageously configured to define the corresponding border line 39 between the two region of sonographic image 37, for each ultrasound propagation line $15_i$, at such time $t_2$.

Computer 24 comprises, according to the invention, a program means for extracting a frequency spectrum 42, shown more in detail in FIG. 3, of the reflected signal that comes from points or sites of ROI 37 corresponding to groups of pixels 31 of the portion of sonographic image 29 that corresponds to ROI 37, to be compared with at least one reference or sample or model frequency spectrum 52 shown in FIG. 1B. More In particular, with reference to FIG. 1C, the program means allows to extract a plurality of frequency spectra $43_i, 44_i$ that are associated with respective segments of ultrasound propagation lines $15_i$, of ROI 37. In particular, in FIG. 1C the spectra $43_i$, are associated with two segments of a portion of ROI 37 in the cortical region 40', whereas the spectra $44_i$, pertain to two segments of a portion of ROI 37 in the trabecular region 41', as shown in FIG. 1.

Frequency spectra $43_i, 44_i$ can be obtained from the data shown on the left hand of the time plot of FIG. 1C, and shown more in detail in FIG. 2, via a well-known transformation 46 (as indicated by the white arrow in FIG. 1C) in the frequency domain, for example via a Fast Fourier Transform (FFT).

Frequency spectrum 42 of FIG. 3 has a smooth trend similar to that of a spectrum $43_i$ that is obtained from the raw reflected signals coming from points of cortical region 41', however, in the following part of the description, reference is made to this spectrum 42 indifferently relating to spectra $43_i$ or $44_i$ obtained by signals reflected by points 34 respectively of cortical part 40' and of trabecular part 41' of bone region 21. In the following part of the description, as explained, frequency spectrum 42 of FIG. 3 can also be an average spectrum calculated on the whole ROI 37 of FIG. 1.

Spectrum 42 of FIG. 3 shows a signal intensity A for each value of the frequency v. In particular, in case of raw reflected signals coming from a point 34 of ROI 37, for each value of the frequency v the intensity is shown of a portion of this raw reflected signal that has this frequency v. In other words, frequency spectrum 42 comprises a plurality of harmonic components in which, to each frequency v of the frequency band, the intensity A of a portion of the reflected signal that has the same frequency is associated.

In an exemplary embodiment of apparatus 100, the space selection means of apparatus 100 comprises a program means for checking and/or for defining the surface or interface 27 of bone region 21. This is helpful for the investigation of bones that have a shape complicated by the presence of bone protrusions or processes, which are normally unimportant for the purpose of assessing the patient's bone structure condition, since they have no mechanical resistance function, as in the case of the spinous processes of the vertebrae. Such bone processes affect the acquisition of reflected signals in the case of a dorsal approach to the vertebrae, which is specially required in the case of particularly fat patients who have a thick layer of soft tissues, abdominally with respect to the vertebrae, in particular to the lumbar vertebrae.

As shown in FIG. 1, in an exemplary embodiment of apparatus 100, computer 24 comprises a program means for extracting a frequency spectrum 47,48 associated with ROI 37, starting from a plurality of spectra $43_i, 44_i$ associated with segments of ultrasound propagation lines $15_i$ of region of interest 37. For example, the spectrum processing means may calculate the mean frequency spectrum 47, 48 (FIG. 1D) as an arithmetic average 49 of spectra $43_i, 44_i$ of FIG. 1C associated with the segments of ultrasound propagation lines $15_i$ of FIG. 1. The program means of computer 24 may be configured to calculate an average spectrum 47 on the portion of ROI 37 that corresponds to a domain of cortical part 40' of bone region 21, starting from frequency spectra $43_i$ associated with segments of ultrasound propagation lines that comprise points of cortical part 40', and/or it may be configured to calculate an average spectrum 48 on the portion of ROI 37 corresponding to a domain of trabecular part 41' of bone region 21, starting from the frequency spectra $44_i$ associated with segments of ultrasound propagation lines corresponding to points of trabecular part 41'. The frequency spectra 47, 48 can be interpreted the same way as the frequency spectra associated with portions of the ultrasound propagation lines 151, i.e. they provide the amplitude value a of a mean signal coming from the cortical and trabecular portions of ROI 37, respectively, for a given value of the frequency v (FIG. 3).

In an exemplary embodiment of apparatus 100, computer 24 comprises a program means for carrying out a compensation of the mean frequency spectrum 47,48 on a segment of an ultrasound propagation line $15_i$ or on ROI 37. In particular, the compensation is carried out by multiplying the reflected signal intensity of each of the harmonics, that correspond to respective frequencies v, for a respective compensation coefficient, the compensation coefficient increasing responsive to the frequency v from 1, which corresponds to the nominal frequency v*, up to a maximum value, which corresponds to a frequency different from the nominal value. The compensation coefficient can be obtained from the transfer function of ultrasound probe 11, i.e. from the sensitivity characteristics of probe 11.

In an exemplary embodiment of apparatus 100, computer 24 comprises a program means for calculating the mean frequency spectrum pertaining to a volume of bone region 21, not shown, starting from average spectra 47,48 of regions of interest of a plurality of sonographic planes, in particular calculating an average spectrum of average spectra 47,48 of plane regions of interest of sonographic planes, such as plane 17.

In an exemplary embodiment of apparatus 100, computer 24 comprises a program means for executing a normalization of spectra $43_i, 44_i$ associated with segments of an ultrasound propagation line $15_i$, and/or a normalization of mean frequency spectrum 47,48 of a ROI 37 by shifting such frequency spectrum/spectra $43_i, 44_i, 47, 48$ in such a way that the maximum value of the intensity of the spectrum/spectra becomes 0, therefore the intensity values lower than the maximum value become negative values, typically expressed in dB.

Computer 24 of apparatus 100, according to the invention, comprises a means for comparing a calculated frequency spectrum, for example each of the spectra $43_i, 44_i$ associated with segments of ultrasound propagation lines $15_i$, and/or for comparing an average spectrum 47,48, with at least one reference spectrum of a healthy subject and/or of a pathological subject. To this purpose, in an exemplary embodiment, computer 24 has an access to a database 51 of reference spectra or models 52 and/or of reference parameters values of such spectra pertaining to healthy subjects and/or to pathological subjects according to a predetermined seriousness of a bone disease, in particular of an osteoporotic disease. Preferably, the computer is configured to select in this database at least one spectrum and/or at least one reference parameter pertaining to a category of the same sex, or of the same age range, or of the same ethnic origin, or of a same particular comorbid condition, or that has another same significant relevance for the patient. This access may comprise a connection to a local or to a remote server, as well as a conventional connection means, in particular a telecommunication network.

According to an aspect of the invention, a calculation means is associated to the comparison means for calculating at least one diagnostic parameter that describes the patient's bone structure condition with respect to healthy subjects and/or with respect to pathological subjects and/or with respect to pathological subjects who suffer from a bone disease of a determined seriousness.

In particular, the diagnostic parameter can be correlated to the bone mineral density, on the basis of reference tests performed by devices that are considered the "gold standard", for example X-ray devices.

In an exemplary embodiment of apparatus 100, computer 24 comprises a program means for calculating the reference parameter for comparing a patient's spectrum $43_i,44_i,47,48$ with a spectrum taken from database 51, such as a shape parameter of spectrum $43_i,44_i,47,48$ or a combination of shape parameters. As shown in FIG. 3, the shape parameters may be:

- an area 53 defined by the frequency spectrum in a predetermined range 54 of frequencies v or in a predetermined range 55 of amplitudes A;
- a width 54 of the frequency spectrum at a prefixed level 56 of the amplitude A, in particular at a level that is defined by an amplitude value 56 that is lower than a maximum value 57 of frequency spectrum 42 by a predetermined amount 55;
- a frequency 58 corresponding to a maximum value 57 of frequency spectrum 42;
- a slope 59, i.e. the inclination, of a line 60 that interpolates a plurality of points 61 of frequency spectrum 42 in a predetermined range 62 of frequencies v;
- the coefficient of a polynomial function corresponding to a curve 64 that interpolates a plurality of points 66 of a frequency spectrum 42 in a frequency range 65 that contains the frequency 57 corresponding to a maximum value of frequency spectrum 42;
- a combination, in particular a ratio of physical quantities that can be deduced from the frequency spectrum, for example the above indicated physical quantities 53,54, 58,59;

considered each alone and/or in combination with one another.

The means for calculating at least one diagnostic parameter can be configured to calculate another desired parameter that is adapted to describe the shape of spectrum 42 or of a mathematical representation thereof, for instance a representation of the spectrum by means of such a method as IC, Wavelet, and the like.

In an exemplary embodiment of apparatus 100, computer 24 comprises a comparison and calculation means configured to:

- calculate at least one correlation coefficient with a frequency spectrum $43_i,44_i$, pertaining to a segment of an ultrasound propagation line $15_i$ and/or an average spectrum 47,48 calculated on ROI 37, or on a portion thereof, and a reference spectrum, or a corresponding portion, of a healthy subject and/or of a pathological subject, and/or of at least one pathological subject who suffers from a bone disease of a predetermined seriousness, and to
- calculate the diagnostic parameter starting from this correlation coefficient.

In particular, the comparison and calculation means is configured to calculate a Pearson's correlation coefficient.

Example 1—Construction of the Model

In order to identify the osteoporotic model of a determined category, which is defined as a combination of race, sex, age and body mass index, the data of the most osteoporotic patient are initially considered, which is defined by a T-score minimum value calculated by DXA, typically a value<−3.5, among the patients of the database who belong to a determined category. The data of this patient are computed by the algorithm given hereinafter, by which a final average spectrum M* is obtained that can be averaged out together with the corresponding final spectra M* of further patients that are to be included in the model, in particular these further patients can be two further patients that have T-score values set between −3.5 and −3.0, and between −3.0 and −2.5, respectively.

In order to create the healthy models a similar procedure is followed, with a "healthiest" patient who typically has a DXA T-score>0 and possibly with two further patients who have T-score values set between −0.5 and 0 and between −0.5 and −1.0, respectively.

Once a subject has been selected to be included in a predetermined osteoporotic or healthy model of a specific category, the following procedure is followed:

a) selecting a sonographic frame that contains the image of a vertebra (typically, of a lumbar vertebra);
b) performing the above described analysis procedure until single compensated and normalized trabecular spectra $S_i$ are obtained:
- defining the interface of the vertebra to be investigated and a bundle of ultrasound propagation lines (typically some dozens) that meet the defined interface;
- on each radiofrequency signal that is associated with one ultrasound propagation line of the above bundle, selecting a portion corresponding to the reflection provided by a trabecular region of the bone;
- computing the spectrum (FFT) for each of the above signal portions;
- "compensating" each spectrum in order to take into account the characteristics of the receiving range of the probe;
- normalizing each spectrum with respect to the maximum value of the spectrum itself (so that the maximum value becomes 0 dB; each of these spectra is indicated here by the reference Si);
c) computing the average spectrum M0 of all the single spectra Si that have been calculated;
d) for each spectrum Si that was obtained at the end of step b), computing the Pearson's correlation coefficient (r) between spectrum $S_i$ and the average spectrum M0;
e) among all the spectra $S_i$ that were obtained at the end of step b), selecting the spectra $S1_i$ that have r>0.900, with respect to average spectrum M0;
f) computing the average spectrum M1 of the spectra $S1_i$ selected in step e);
g) for each spectrum $S_i$ obtained at the end of step b), computing the Pearson's correlation coefficient between this spectrum $S_i$ and the average spectrum M1;
h) Among all the spectra $S_i$ that were obtained at the end of step b), selecting the spectra $S2_i$ that have r>0.900 with respect to the average spectrum M1 (N.B.: the number of spectra $S2_i$ can be higher than, lower than or the same as the number of spectra $S1_i$ that were obtained in step e);
i) computing the average spectrum M2 of to the spectra $S2_i$ selected in step h);
j) repeating the cycle comprising the steps g), h), i) until an average spectrum Mn is obtained that satisfies both the following conditions: a) each spectra $Sn_i$ that is included in the average spectrum Mn has r>0.900 with respect to Mn; b) each further spectra that is not included in the average Mn has r≤0.900 with respect to Mn (in other words, the procedure stops when a further repetition of the procedure would give a spectrum Mn+1 that is coincident with the last calculated Mn);

k) repeating the points a)-i) for other three vertebrae (typically lumbar vertebrae), thus obtaining 4 Mn-type spectra, one for each observed vertebra;

l) computing the average spectrum M* of these 4 spectra Mn.

Spectrum M* represents the contribution of the single subject to the above model $M^*_{TOT}$, obtained from the average of all the M* of the subjects that are included in the model of the corresponding category.

The operation of apparatus 100 according to the invention is now described with reference to the block diagram of FIG. 4, which shows a first procedure 400 for assessing the bone condition of a patient, in particular the bone structure condition and/or a bone mineral density with reference to a specific bone region 21 (FIG. 1).

Procedure 400 comprises a preliminary step 101 of pre-arranging a sonographic device i.e. a probe 11 (FIG. 1), close to the patient's bone region 21, so that probe 11 can receive raw ultrasound signals 36,38 that are reflected by bone region 21 in response to ultrasound pulses coming from probe 11. The operation of apparatus 100 comprises the subsequent steps of:

generating and transmitting 110 an ultrasound signal 13 through ultrasound probe 11 towards bone region 21 during a predetermined emission time 25, such that bone region 21 returns raw reflected ultrasound signals 36, 38, in response to emitted ultrasound signal 13;

creating 120 a sonographic image 29 of bone region 21 by associating the intensity of each raw reflected ultrasound signal 36,38 coming from a respective point 33 of a portion of bone region 21, with an image parameter, for instance with a gray scale level;

possibly defining 130 a region of interest 37 of bone region 21 on sonographic image 29, for example by selecting an area 37 of image 29 as this is shown by a display apparatus 35 of a computer 24, using a conventional image selection means, or an automatic process of defining/recognizing ROI 37 by computer 24;

calculating 140 frequency spectra 42 on the basis of raw reflected signals coming from bone region 21 or, possibly, from region of interest 37. Frequency spectrum 42 (FIG. 3) comprises a plurality of harmonics in which the intensity A of a portion of the reflected signal that has a frequency v of the frequency range is associated to this frequency v, by transforming the reflected signal into the frequency domain. The transformation 46 can be carried out by well-known techniques, for instance, by Fast Fourier Transform. In particular, the frequency spectra extraction means is configured to carry out this transformation on reflected ultrasound signals that come from points 34 of respective segments of ultrasound propagation lines $15_i$ within bone region 21 or ROI 37, in order to obtain overall frequency spectra that are responsive to respective segments of ultrasound propagation lines;

comparing 150 a frequency spectrum 42 with at least one reference spectrum that is associated with at least one healthy subject-model and/or one pathological subject-model, and calculating a diagnostic parameter on the basis of the comparison. The reference spectrum or reference spectra may be the result of a database search step 149, possibly using reference search parameters that identify a category including at least one feature of the patient, selected among the sex, the age range, the ethnic origin, a particular comorbid condition, as well as any other significant category.

If bone portions need to be investigated which cannot be easily observed due to bone protrusions or processes of no mechanical importance and/or of no importance for the investigation, a means is also provided for performing a step 105 of defining an interface 27 of bone region 21 on a first sonographic image (FIG. 1). For example, in the case of a posterior approach to lumbar vertebrae, a first sonographic acquisition 110-120 can be used to identify the bone processes and to set a correction procedure such that the subsequent acquisition/s puts/put aside these bone portions, i.e. put/s aside the reflected signals received after a time shorter than a prefixed time threshold corresponding to the surface or to the interface of bone region 21 to be investigated.

In a particular operation mode of apparatus 100, a means may be provided for performing a step, not shown in FIG. 4, of filtering the range of frequencies such that bone region 21 receives signals that have only frequencies of a range of predetermined amplitude, narrower than the amplitude range of probe 11.

Procedure 400 may also comprise a step 141 of compensating the frequency spectra $43_i,44_i$ that are associated with segments of ultrasound propagation line $15_i$, or of compensating the frequency spectra 47,48 associated or obtained as average spectra on bone region 21 or on ROI 37. In particular, this is useful for taking into account the features of the receiving range of probe 11, for example as described above.

Procedure 400 may also comprise a step 142 of normalizing frequency spectra $43_i,44_i$ that are associated with segments of ultrasound propagation line $15_i$ or normalizing the frequency spectra 47,48 associated or obtained as average spectra on bone region 21 or on ROI 37 with respect to the respective maximal values, so that the maximum amplitude value of such spectra becomes 0 dB. This simplifies the subsequent calculation of the shape parameters of the frequency spectra.

Block diagram of FIG. 5 shows a procedure 500 that is a first particular operation mode of apparatus 100. Also operation mode 500 comprises steps 101-130 shown in the diagram of FIG. 4. In operation mode 500, the calculation step 140 of the spectrum comprises a step 145 of calculating spectra $43_i$ and/or $44_i$ associated with segments of ultrasound propagation lines $15_i$, which are defined by the sonographic crystals of probe 11, and a step 146 of computing an average spectrum 47 and/or 48 on ROI 37, starting from spectra $43_i$ and/or $44_i$. For each frequency v, the average value of intensities A is measured at this frequency v on the single spectra $43_i$ and/or $44_i$. The calculation step 145 of the spectra associated with segments of ultrasound propagation lines may provide spectra $43_i$ that are associated with segments of ultrasound propagation lines 151 in cortical part 40' of bone region 21. In alternative, or in addition, the calculation step 145 may provide spectra $44_i$ that are associated with portions of respective ultrasound propagation lines $15_i$ in trabecular part 41' of bone region 21. Therefore, an average spectrum 47 on the cortical part and/or an average spectrum 48 on the trabecular part of ROI 37 are provided. Even if in FIG. 5 the steps of compensation 141 and of normalization 142 are not shown, both or either the steps can advantageously be carried out after the step of computing each partial spectrum $43_i$ and/or $44_i$.

Always in operation mode 500, the step 150 of comparing and computing a diagnostic parameter comprises step 153 of computing at least one shape parameter, for example at least one of the above shape parameters 53,54,58,59, or of computing other significant parameters. The comparison and calculation step 150 may comprise a step 154 of computing a complex shape parameter as a combination of these diagnostic parameters, and a step 155 of comparing the diagnostic parameters obtained from the shape parameters, and/or possibly from a combination thereof, with corresponding diagnostic parameters of cortical and/or trabecular spectra of a healthy subject. The parameters of the healthy subject may be retrieved by a search step 149 like step 149 of FIG. 4, which is not shown in the diagram of FIG. 5 for the sake of simplicity. An example of complex shape parameter is obtained by adding −1 dB to the width of the cortical spectrum and by adding −3 dB to the width of the trabecular spectrum.

Briefly, according to the operation mode or algorithm 500 of FIG. 5, the diagnostic parameter, which is an index of the quality of the bone tissue of bone region 21 that has been investigated, is calculated as a shape parameter that characterizes the mean frequency spectrum 47,48 of the reflected ultrasound signals as reflected by ROI 37, i.e. by a determined portion of bone region 21.

Block diagram of FIG. 6 shows a process 600 that is a second particular operation mode of apparatus 100. Also this operation mode comprises steps 101-130 shown in the diagram of FIG. 4, which is present also in the process or algorithm shown in FIG. 5.

In this case, spectra computation step 140 is limited to a step of computing spectra $43_i$ and $44_i$ that are associated with segments of ultrasound propagation lines $15_i$. The spectra computation step 145 may provide spectra $43_i$ associated with segments of ultrasound propagation lines $15_i$ that are included in cortical part 40'. In alternative, or in addition, the spectra computation step 145 may provide spectra $44_i$ associated with portions of respective ultrasound propagation lines $15_i$ in trabecular part 41' of bone region 21. Even if in FIG. 6 the compensation step 141 and normalization step 142 are not shown, both or either the steps can advantageously be carried out after the step of computing each partial spectrum $43_i$ and/or $44_i$.

Also in the case of process 600, step 150 of comparing and computing a diagnostic parameter provides preliminarily a step 149 of searching reference spectra or models of a healthy and/or pathological subject shown in FIG. 4. This step is not shown in the diagram of FIG. 6 for the sake of simplicity. Step 150 of comparison and calculation comprises a step 156 of computing a correlation coefficient r with at least one spectrum model 52 selected among a "healthy" spectrum model, a "pathological" spectrum model and preferably also an "intermediate" spectrum model. In this calculation step 156, the correlation coefficient that is calculated may be, for instance, the Pearson's correlation coefficient.

A step 157 follows of validating/rejecting sonographic spectra, wherein each spectrum is considered valid if at least one of the correlation coefficients r, that are calculated with respect to the healthy model, or to the pathological model or to the intermediate model, is higher than or the same as a predetermined minimum threshold value. For example, it may happen that at least one of the calculated Pearson's coefficients is higher than 0.75. Otherwise, this spectrum is considered invalid and is rejected, i.e. it is not taken into account in the prosecution of the analysis.

A following evaluation or classification step 158, may comprise computing the ratio of frequency spectra $43_i$, $44_i$ that have a correlation coefficient with the healthy models, with the intermediate models and with the pathological models, higher than the predetermined minimum threshold value. In the classification step 158, each spectrum that has been evaluated as valid is classified as "healthy" or as "osteoporotic" depending upon whether the respective correlation coefficient with the healthy model is higher than the respective correlation coefficient with the "osteoporotic model", or vice-versa. If these two values of r are substantially the same value, for example to the third digit after the point, the spectrum is considered invalid.

In a following step 159 of defining and computing a diagnostic parameter, the percentage of healthy spectra over the number of valid spectra may be selected as a diagnostic parameter. Actually, in an investigation in which 90% of the spectra have a correlation coefficient higher than the threshold value, the complement to 1 of this ratio, i.e. 0.1, can be selected as a diagnostic parameter. The lower this diagnostic parameter, the healthier is the subject.

In the step 159 of defining and computing the diagnostic parameter, it is also possible to define a more specific diagnostic parameter, i.e. a diagnostic parameter that takes into account the values of the correlation coefficient that are considered valid. For instance, the arithmetic mean value of the correlation parameter of the healthy spectra can be defined as a diagnostic parameter, or a combination of statistic parameters that describe the distribution of such correlation coefficients.

In the analysis, the frequency spectra $43_i$ pertaining to cortical portions of bone region 21, and/or the frequency spectra pertaining to trabecular portions $44_i$, may be taken into account and the spectra pertaining to cortical portions and to trabecular portions can be considered together, or separate.

In another operation mode of the apparatus, once a region has been classified as a healthy region, or as a pathological region, or as an intermediate region, according to the percentage of spectra that is classified as healthy, positive or intermediate, step 156 may comprise computing the correlation coefficient between each spectrum and the reference spectra that pertain to specific pathology values or levels, i.e. to healthy or pathological or intermediate spectra, to which specific diagnostic parameters are associated. In this case, the subsequent step 159 of defining and computing a diagnostic parameter comprises selecting the value of the diagnostic parameter of the reference spectrum that indicates the best correlation with the valid spectra as a diagnostic parameter that describes the bone region of the investigation.

In the case of a vertebral investigation, the result can be made more reliable if a plurality of vertebrae is considered, according to how higher is the percentage of spectra that correlate with a healthy, or with a pathological or with an intermediate model. The result might be rejected if the total percentage is too low, in which case a new acquisition is required.

Algorithms 500 and 600, which are shown in FIG. 5 and in FIG. 6, respectively, provide a value of a diagnostic parameter for each vertebra that has been taken into account, as an output. In an operation mode, the procedure is carried out for a plurality of vertebrae, typically a plurality of lumbar vertebrae, for instance four adjacent vertebrae, and the average value of the results pertaining to this plurality of vertebrae can be selected as the patient's diagnostic parameter.

The diagnostic parameter, or a further diagnostic parameter, may be calculated as a parameter selected between T-score and Z-score, where:

T-score is calculated by computing the difference between the value of the diagnostic parameter (BMD) and the average value (BMD)' of the same parameter measured for subjects of the same sex, but of an age at which the peak bone mass value occurs (typically 30 years), and dividing the result of this difference by the standard deviation σ' of the values of the parameter measured for the subjects at their peak bone mass value, i.e. T-score is calculated by the formula:

$$T\text{-score}=[(BMD)-(BMD)']/\sigma'$$

Z-score is calculated by computing the difference between the value of the diagnostic parameter (BMD) and the average value (BMD)" of the same parameter measured for subjects of the same sex and of the same age of the patient, and dividing the result of this difference by the standard deviation a" of the values of the parameter measured for the subjects of the same age, i.e. Z-score is calculated by the formula:

$$Z\text{-score}=[(BMD)-(BMD)'']/\sigma''$$

In this case, the disease condition may be classified according to the definition of the World Health Organization (WHO), based on the T-score value:

T-score>−1: normal bone mineral density, i.e. absence of signs of disease;

−2.5<T-score<−1: osteopenia, i.e. the skeleton has a reduced mineral bone density with respect to the peak bone mass value, but an overt osteoporosis is not yet present;

T-score<−2.5: osteoporosis.

Example 2

An example of a way to carry out process 600 of FIG. 6 is given hereinafter. 275 white women were selected whose age was between 45 and 75 years, and who had different body mass index or BMI. The 275 women were grouped into 11 categories according to the age and to the BMI, as shown in table 1:

TABLE 1

| Category N. | Age range years old | BMI range kg/m² | Numerosity |
|---|---|---|---|
| 1 | 46-50 | <25 | 30 |
| 2 | 51-55 | <25 | 44 |
| 3 | 56-60 | <25 | 47 |
| 4 | 56-60 | 25-30 | 36 |
| 5 | 56-60 | >30 | 8 |
| 6 | 61-65 | <25 | 30 |
| 7 | 61-65 | 25-30 | 31 |
| 8 | 61-65 | >30 | 12 |
| 9 | 66-70 | <25 | 13 |
| 10 | 71-75 | 25-30 | 15 |
| 11 | 71-75 | >30 | 9 |

The 275 subjects included in the study were subjected to DXA, and were classified as "osteoporotic", "osteopenic", "healthy" according to whether T-score≤−2.5; −2.5<T-score<−1; T-score≥−1, respectively. For each of the 11 categories a maximum of 3 subjects was taken to be used in the osteoporotic model, and a maximum of 3 subjects was taken to be used in the healthy model, operating as described in the Example 1.

Once the models had been calculated for all the categories, four sonographic images were selected for each of the 275 subject included in the study, one image for each vertebra of the segment L1-L4. Each image was analyzed, along with the corresponding "raw" radiofrequency, by algorithm 600 of FIG. 6, described above, following these restrictions:

only trabecular spectra were considered;

in step 157 of validating/rejecting the spectra, only the spectra which had a Pearson's correlation coefficient r>0.75 with at least one of the two models for the same patient category were classed as "valid" spectra;

in the step 158 of classifying the valid spectra:

the spectra for which the correlation coefficient r with the relative osteoporotic model was higher than the correlation coefficient with the healthy model were classified as osteoporotic;

the spectra for which the correlation value with the healthy model was higher than the correlation value with the osteoporotic model were classified as healthy;

whereas the spectra for which the values of the correlation coefficients with both models were the same value up to the third digit after the point were classified as "invalid" and were rejected;

for each vertebra, a diagnostic parameter (step 159) was then defined and calculated as the percentage of valid spectra that had been classified as osteoporotic, over the total of the valid spectra of that vertebra;

for each subject included in the study, the average value of the diagnostic parameters of the four vertebrae was selected as the diagnostic parameter which then is also expressed as the percentage of osteoporotic spectra.

Figure 8:
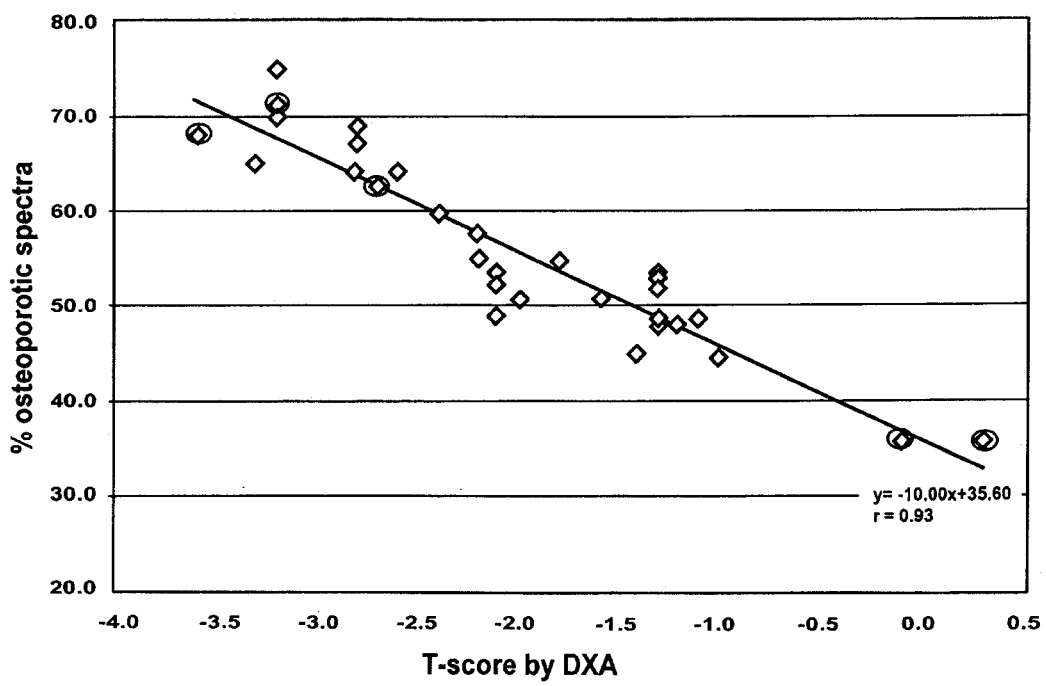
FIGS. 8 and 9 are diagrams of this diagnostic parameter, for the same population of FIG. 7, plotted versus T-score and Z-score, respectively.
Figure 9:
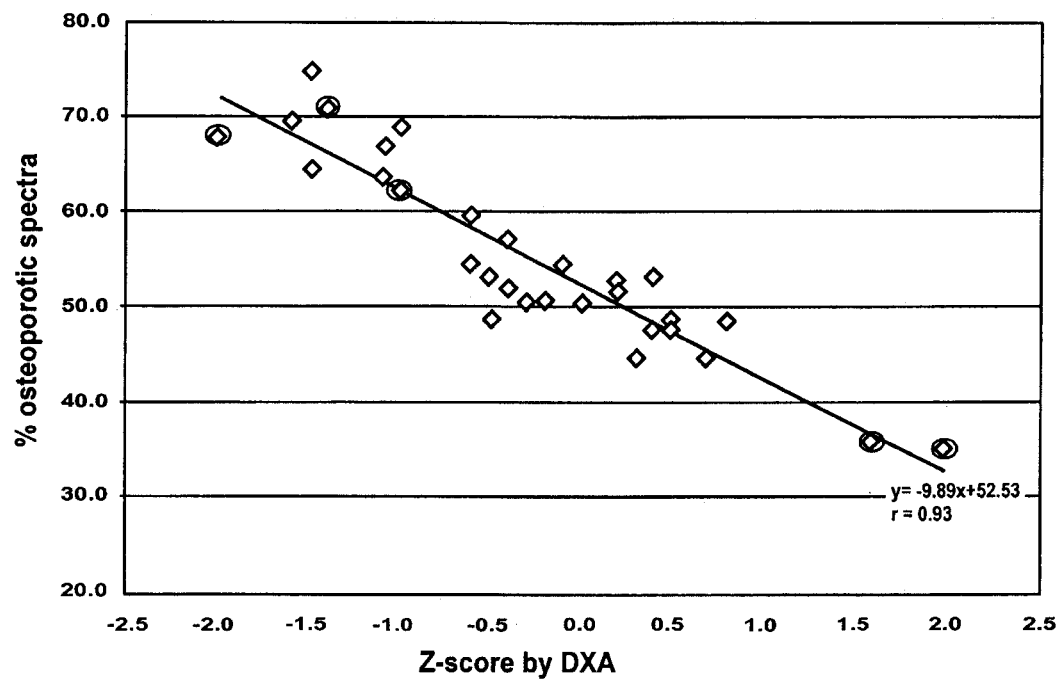

For each of the 11 categories of table 1, the diagnostic parameter was plotted against the BMD (bone mineral density) evaluated by the DXA system. For the sake of conciseness, FIG. 7 shows only the diagram of category n. 7 (age 61-65 years, BMI 25-30 kg/m²). The diagnostic parameter was also plotted against the other parameters provided by the DXA system, i.e. the T-score and the Z-score, by comparing the value of the BMD, as measured, with the reference population database. Still with reference to category n. 7, the diagrams are shown in FIG. 8 and in FIG. 9, respectively. In the diagrams of FIGS. 7-9, the symbols surrounded by a circle identify the subjects whose data were used to calculate the model spectra of the same category, in particular three subjects were used for the osteoporotic model and two subjects were used for the healthy model.

From the diagrams of FIGS. 7-9, it can be noticed that the calculated diagnostic parameter, i.e. the percentage of valid spectra classified as osteoporotic over the total of the valid spectra, shows a quite good linear correlation with a Pearson's coefficient r of 0.93, with all three parameters provided by the DXA system.

Furthermore, the diagnostic parameter is particularly suitable for discriminating between healthy, osteopenic and osteoporotic subjects. In fact, with reference to FIG. 8, it can be observed that:

the osteoporotic subjects (T-score≤−2.5) are characterized by a percentage of osteoporotic spectra≥60% and, similarly, the osteopenic subjects (−2.5<T-score<−1) are characterized by percentage of osteoporotic spectra set between 45% and 60%, and the healthy subjects (T-score have a percentage of osteoporotic spectra lower than 45%.

Similar results were obtained for all the other categories that were taken into account.

The equations of the approximation lines, which are depicted on each diagram of FIG. 7-9, can be used, after inversion with respect to the abscissa axis, to evaluate the BMD values, the T-score and the Z-score, starting from the value of the diagnostic parameter. For instance, still with reference to category n.7, for a subject for which a percentage of osteoporotic spectra of the 64.0%, was obtained, we have:

$$BMD = \frac{130.25 - 64.0}{90.31} = 0.734 \text{g/cm}^2$$

$$T-\text{score} = \frac{35.60 - 64.0}{10.00} = -2.8$$

$$Z-\text{score} = \frac{52.53 - 64.0}{9.89} = -1.2$$

Figure 10:
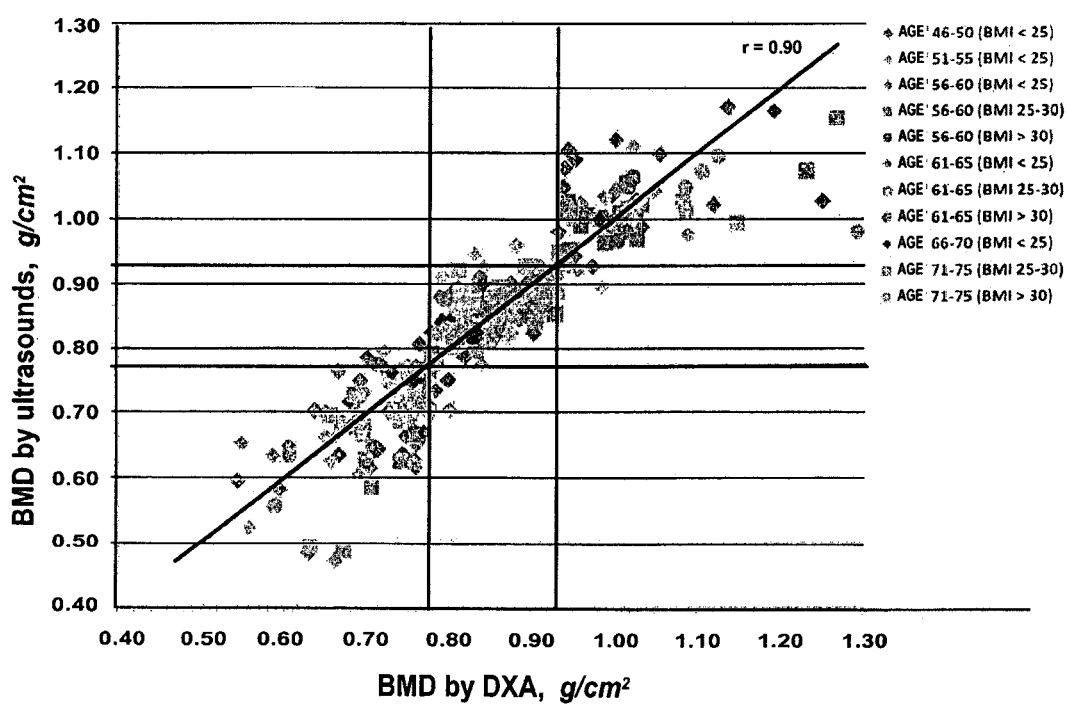
Figure 11:
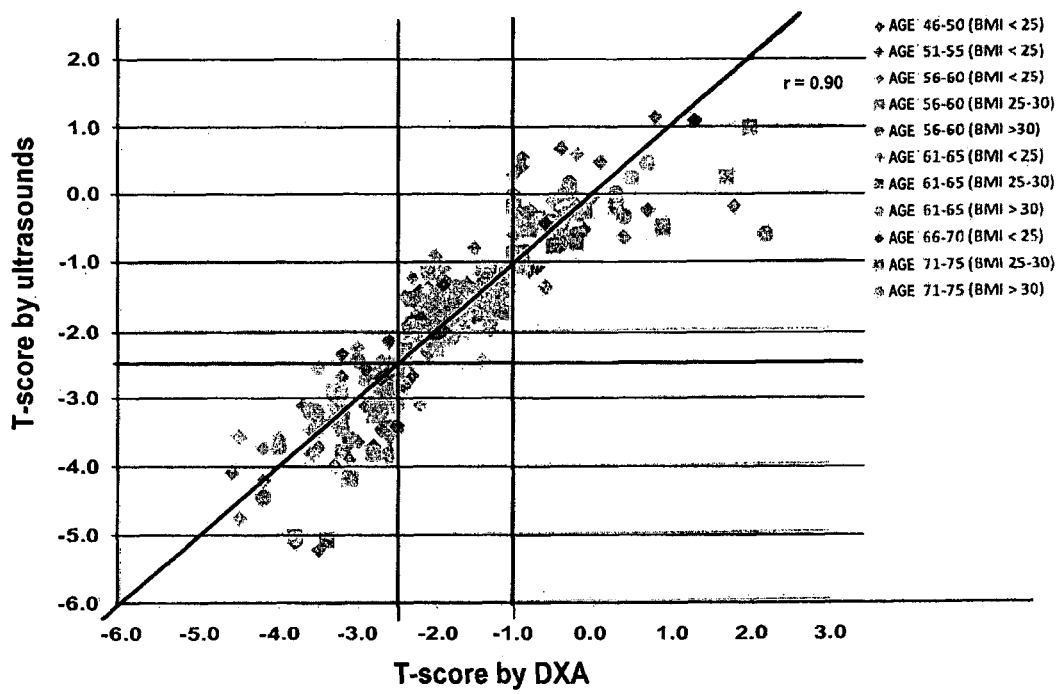
Figure 12:
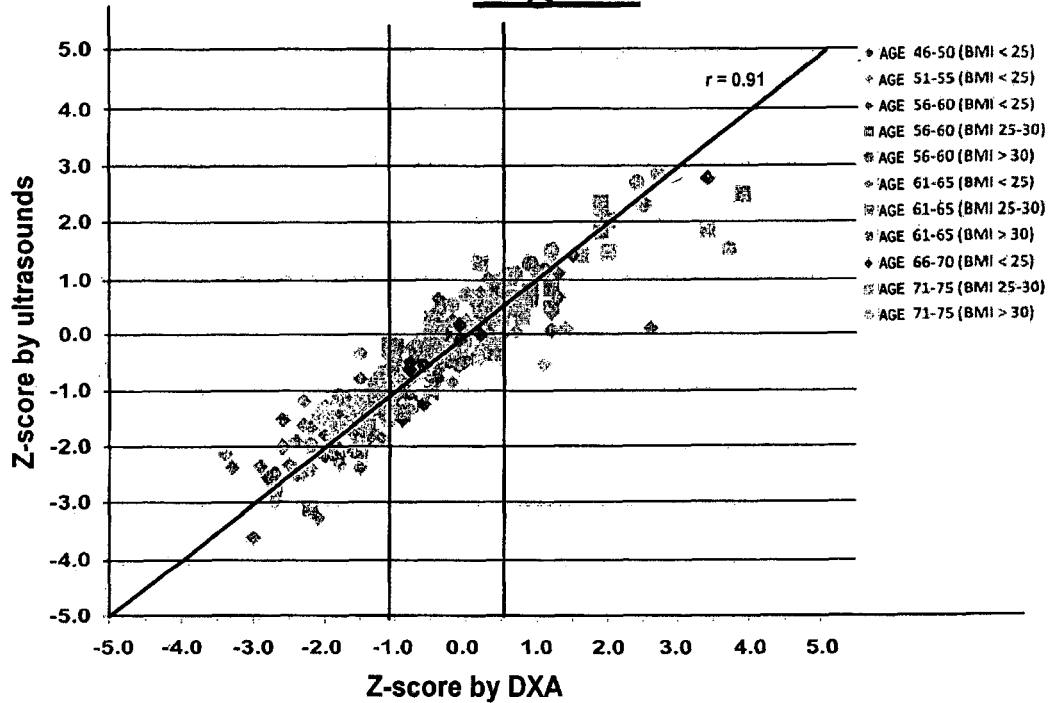
Figure 13:
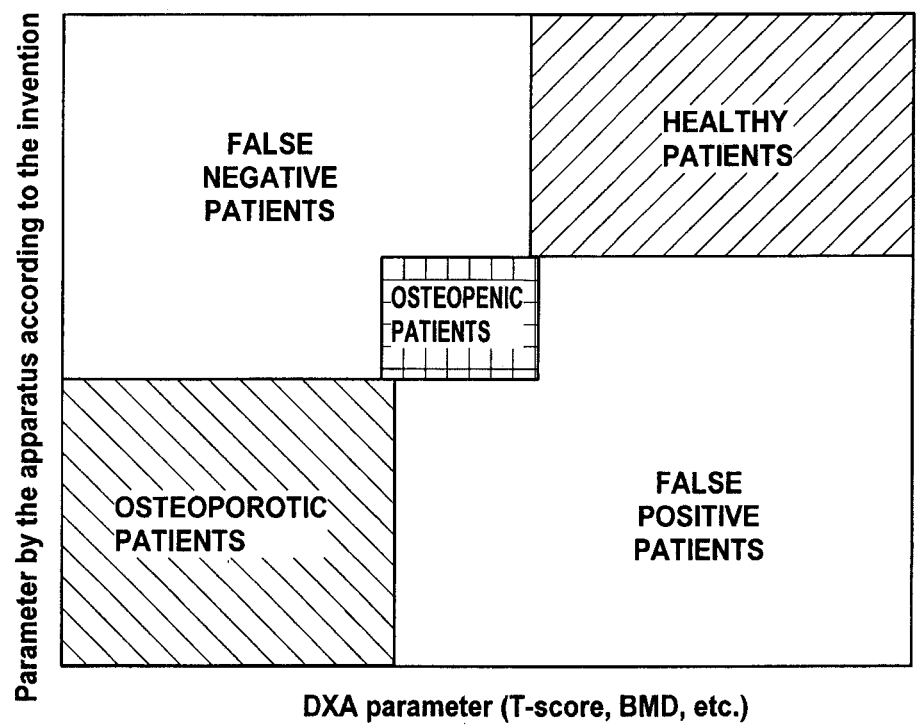
FIG. 13 is a diagram that summarizes the diagrams of FIGS. 10-12.

By repeating the calculus for all the subjects that were investigated, and for all the categories, the results of FIGS. 10, 11 and 12 were obtained, which resume the evaluations that were performed by the apparatus according to the invention. These evaluations were correlated with the respective DXA parameters. The diagrams of FIGS. 10, 11 and 12 show a good correlation between the data, as described hereinafter. FIG. 13 contains a summarizing diagram of those of FIGS. 10-12, which simplifies their interpretation. The results are also resumed in table 2.

TABLE 2

|  | Tested cases | wrong diagnosis vs DXA |
|---|---|---|
| BMI < 25 | 164 | 9 (5.5%) |
| 25 < BMI < 30 | 82 | 0 (0.0%) |
| BMI > 30 | 29 | 0 (0.0%) |
| TOTAL | 275 | 9 (3.3%) |

Age range: 45-75 years

From table 2 and from FIGS. 10 and 11, it can be observed that the few diagnostic cases that appear to be unaligned between the two methods always pertain to "osteopenic" cases who are classified as healthy, or vice-versa, or as osteoporotic or vice-versa, while in no case a healthy subject was classified as osteoporotic, or vice-versa.

Accuracy values of the three parameters BMD, T-score and Z-score were also calculated as the mean error±standard deviation, which confirm the good reliability of process 600.
BMD=−0.34%±7.42%;
T-score=−0.03±0.56;
Z-score=+0.02±0.52.

Similar conclusions can be drawn by evaluating the same population by procedure 500.

The foregoing description of exemplary embodiments of the apparatus according to the invention, and of the way of using the apparatus, integrally to the examples, will so fully reveal the invention according to the conceptual point of view, so that others, by applying current knowledge, will be able to modify and/or adapt in various applications the specific exemplary embodiments without further research and without parting from the invention, and, then it is meant that such adaptations and modifications will have to be considered as equivalent to the specific embodiments. The means and the materials to realize the different functions described herein could have a different nature without, for this reason, departing from the field of the invention. It is to be understood that the phraseology or terminology that is employed herein is for the purpose of description and not of limitation.

The invention claimed is:

1. An apparatus (100) for assessing a condition of bone tissue in a patient's bone region (21), said apparatus (100) comprising:
an ultrasound device provided with an ultrasound probe (11) having an array of piezoelectric crystals that is configured to emit ultrasound pulses having a nominal frequency set between 2 and 9 MHz along a plurality of ultrasound propagation lines ($15_i$) arranged in a sonographic plane (17) forming an ultrasound signal that can reach said patient's bone region (21), and to receive first raw ultrasound signals (36) reflected from a cortical part (40') of said patient's bone region (21) and second raw ultrasound signals (38) reflected from a trabecular part (41') of said patient's bone region (21), in response to said ultrasound pulses;
said ultrasound probe (11) configured to emit said ultrasound pulses during a prefixed emission time (25), said ultrasound probe (11) is arranged to transmit said ultrasound pulses and to receive said first raw ultrasound signals (36) reflected from the cortical part (40') of said patient's bone region (21) and said second raw ultrasound signals (38) reflected from the trabecular part (41') from a same side of said patient's bone region (21), such that said first raw ultrasound signals (36) reflected from the cortical part (40') and said second raw ultrasound signals (38) reflected from the trabecular part (41') are reflected by said bone region (21);
a computer (24) configured to form a sonographic image (29) of a plane cross section of the bone region (21), taken along the sonographic plane (17) starting from said first raw ultrasound signals (36) reflected from the cortical part (40') of said bone region (21) and said second raw ultrasound signals (38) reflected from the trabecular part (41') of said bone region (21), said computer (24) is configured for displaying said sonographic image (29), that identifies a zone of said bone region to be investigated;
wherein said computer (24) is configured to receive and process said first raw ultrasound signals (36) reflected from the cortical part (40') of said bone region (21), and said second raw ultrasound signals (38) reflected from the trabecular part (41') of said bone region (21);
wherein said computer (24) is configured for extracting a plurality of frequency spectra ($43_i$, $44_i$, 47, 48) starting from said first raw ultrasound signals (36) and said second raw ultrasound signals (38) reflected from corresponding points (34) of said patient's bone region (21),
said computer (24) is adapted to determine spectra ($43_i$, 47) associated with segments of ultrasound propagation lines ($15_i$) which are included in cortical part (40') of bone region (21), and spectra ($44_i$, 48) associated with portions of respective ultrasound propagation lines ($15_i$) which are included in the trabecular part (41') of bone region (21);
wherein said computer (24) is configured to memorize:
at least one healthy reference spectrum (52) associated with at least one healthy patient,
at least one intermediate reference spectrum associated with an intermediately-healthy patient,
at least one pathological reference spectrum associated with a pathological patient;
and wherein said computer (24) is configured to calculate respective correlation coefficients of said frequency spectra ($43_i$, $44_i$, 47, 48) associated with said cortical (40') and/or said trabecular (41') parts of said patient's bone region (21), with said memorized:

at least one healthy reference spectrum (52) associated with at least one healthy patient, at least one intermediate reference spectrum associated with an intermediately-healthy patient, at least one pathological reference spectrum associated with a pathological patient and to select, from said frequency spectra ($43_i$, $44_i$, 47, 48) associated with said cortical (40') and/or said trabecular (41') parts of said patient's bone region (21), a number of valid spectra, wherein at least one of said respective correlation coefficients exceeds a predetermined threshold value;

and calculating a percentage of:
  healthy valid spectra over said number of valid spectra,
  intermediate valid spectra over said number of valid spectra,
  pathological valid spectra over said number of valid spectra, wherein each of the valid spectra is a healthy spectrum or a pathological spectrum or an intermediate spectrum according to whether a correlation coefficient with the healthy or with the pathological or with the intermediate reference spectra, respectively, is higher than a correlation coefficient with the other reference spectra, for determining the value of a diagnostic parameter.

2. An apparatus (100) according to claim 1, wherein said correlation coefficients are Pearson's correlation coefficient wherein said predetermined threshold value is between 0.7 and 0.8;

and wherein said computer (24) is configured to
  define a diagnostic parameter selected from the group consisting of:
    said percentage of healthy or pathological or intermediate valid spectra, respectively;
    a parameter according to the average value of said respective Pearson's correlation coefficients of said valid frequency spectra;
    a statistic parameter or a combination of statistic parameters that describe a distribution of values of said respective Pearson's correlation coefficients of said valid spectra;
    a diagnostic parameter associated to a reference spectrum selected among a plurality of reference spectra that represent specific pathology seriousness levels.

3. An apparatus (100) according to claim 2, wherein said threshold value for said Pearson's correlation coefficient is 0.75.

4. An apparatus (100) according to claim 1, wherein said computer (24) is configured to calculate said diagnostic parameter as a shape parameter of said frequency spectra ($43_i$, $44_i$, 47, 48) extracted from said first and second raw ultrasound signals, or as a combination of a plurality of shape parameters of said frequency spectra ($43_i$, $44_i$, 47, 48) extracted from said first and second raw ultrasound signals.

5. An apparatus (100) according to claim 4,
wherein said computer (24) is configured to extract an average frequency spectrum (42) by calculating an average of spectra ($43_i$, $44_i$) that are associated with respective segments of ultrasound propagation lines ($15_i$) included in a region of interest (ROI) and wherein said shape parameter or said shape parameters is/are selected from the group consisting of:
  an area (53) defined by said average frequency spectrum (42) within a predetermined range of frequencies (54) and/or within a predetermined range of amplitudes (55);
  a width (54) of said average frequency spectrum (42) at a predetermined amplitude level (56), in particular at a level defined by an amplitude value (56) which is lower than a maximum value (57) of said average frequency spectrum (42) by 3 dB or by 1 dB;
  a frequency (58) corresponding to a maximum value (57) of said average frequency spectrum (42);
  a slope (59) of a line (60) that interpolates a plurality of points (61) of said average frequency spectrum (42) in a predetermined range of frequencies (62);
  the coefficient of a polynomial that interpolates points (66) of said average frequency spectrum (42) in a frequency range (54) that contains a frequency (58) corresponding to a maximum value (57) of said average frequency spectrum (42).

6. An apparatus (100) according to claim 1, wherein said computer (24) is configured for recognizing and/or defining a limiting surface (27) of said bone region (21), such that a non-significant bone portion or tissue portion can be left out from said patient's bone region (21).

7. An apparatus (100) according to claim 1, wherein said computer (24) is also configured to compute said memorized
  at least one healthy reference spectrum (52) associated with at least one healthy patient,
  at least one intermediate reference spectrum associated with an intermediately-healthy patient,
  at least one pathological reference spectrum associated with a pathological patient;
by the following steps:
  for an healthy patient, an intermediately-healthy patient or a pathological patient: selecting, on a sonographic frame a patient's bone region to be used as a model bone region for the calculation of a healthy reference spectrum, or for the calculation of an intermediate reference spectrum or for the calculation of a pathological reference spectrum;
  generating a bundle of ultrasound signals along a plurality of propagation lines that meet said model bone region;
  on each ultrasound signal reflected by said model bone region, selecting a portion corresponding to a reflection coming from a trabecular region of said model bone region;
  calculating, for each signal of said bundle of ultrasound signals a single spectrum, by FFT (Fast Fourier Transform), for said portion corresponding to a reflection coming from a trabecular region;
  normalizing each of said single spectra with respect to its own maximum value in such a way that its maximum value becomes 0 dB;
  calculating an average spectrum of all said single spectra.

8. An apparatus (100) according to claim 7, wherein said computer (24) for computing said reference spectra is also configured to:
  for each of said single spectra, calculating Pearson's correlation coefficient, between said single spectrum and said average spectrum of all said single spectra;
  selecting each of said single spectra for which the correlation coefficient with the said average spectrum of all said single spectra is larger than the reference value r>0.900;
  calculating a further average spectrum of selected single spectra that have a correlation coefficient higher than r>0.900;
  for each single spectrum calculating a further Pearson's correlation coefficient with said further average spectrum;

among all said single spectra, selecting spectra having a correlation coefficient with the said further average spectrum that is in turn higher than r>0.900;
calculating a further average spectrum of the selected further average spectra;
repeat computing said new correlation coefficient, selecting said single spectra and computing said further correlation coefficients until a final average spectrum is obtained such that:
each single spectrum selected to compute said final average spectrum has-a a correlation coefficient with said final average spectrum higher than r>0.900;
each other spectra not selected to compute said final average spectrum has a correlation coefficient for with said final average spectrum lower than or egual to r<0.900.

9. An apparatus (100) according to claim 7, wherein said computer (24) is configured to:
compute said average spectrum of all said single spectra for four lumbar vertebrae, finally obtaining four average spectra of all said single spectra, one for each of such vertebrae;
calculating a final vertebral average spectrum of the four final spectra.

10. An apparatus (100) according to claim 1, wherein said nominal frequency of emitted ultrasound pulses from said ultrasound probe (11) is selected from the group consisting of 3.5, 5 and 7.5 MHz.

\* \* \* \* \*